(12) United States Patent
Mohapatra et al.

(10) Patent No.: US 7,595,303 B1
(45) Date of Patent: Sep. 29, 2009

(54) GENETIC ADJUVANTS FOR IMMUNOTHERAPY

(75) Inventors: Shyam S. Mohapatra, Tampa, FL (US); Mukesh Kumar, Norwood, MA (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 10/655,873

(22) Filed: Sep. 5, 2003

Related U.S. Application Data

(60) Provisional application No. 60/319,523, filed on Sep. 5, 2002.

(51) Int. Cl.
  *A61K 48/00* (2006.01)
  *A01N 63/00* (2006.01)
(52) U.S. Cl. .................................. 514/44; 424/93.1
(58) Field of Classification Search .................. 514/44; 536/23.1; 435/320.1, 325, 455
  See application file for complete search history.

(56) References Cited

U.S. PATENT DOCUMENTS

| | | | |
|---|---|---|---|
| 4,414,150 A | 11/1983 | Goeddel | |
| 4,456,748 A | 6/1984 | Goeddel | |
| 4,678,751 A | 7/1987 | Goeddel | |
| 4,695,623 A | 9/1987 | Stabinsky | |
| 4,897,471 A | 1/1990 | Stabinsky | |
| 5,571,515 A * | 11/1996 | Scott et al. ............... | 424/208.1 |
| 5,770,191 A | 6/1998 | Johnson et al. | |
| 5,831,062 A | 11/1998 | Taylor | |
| 5,853,755 A | 12/1998 | Foldvari | |
| 6,120,762 A | 9/2000 | Johnson et al. | |
| 6,218,180 B1 | 4/2001 | Kurtzman et al. | |
| 6,489,306 B2 | 12/2002 | Mohapatra et al. | |
| 6,693,086 B1 * | 2/2004 | Dow et al. ..................... | 514/44 |
| 7,052,685 B1 | 5/2006 | Rook | |
| 2001/0006951 A1 | 7/2001 | Mohapatra et al. | |
| 2002/0044919 A1 | 4/2002 | Yu | |
| 2003/0068333 A1 | 4/2003 | Mohapatra et al. | |
| 2003/0138404 A1* | 7/2003 | Maroun ....................... | 424/85.5 |
| 2003/0198624 A1 | 10/2003 | Mohapatra et al. | |
| 2004/0009152 A1 | 1/2004 | Mohapatra et al. | |
| 2005/0025742 A1 | 2/2005 | Engler et al. | |
| 2005/0054052 A1 | 3/2005 | Carr et al. | |
| 2005/0054053 A1 | 3/2005 | Aguinaldo et al. | |
| 2005/0084478 A1 | 4/2005 | Liu et al. | |
| 2005/0266093 A1 | 12/2005 | Mohapatra | |
| 2005/0272650 A1 | 12/2005 | Mohapatra | |

FOREIGN PATENT DOCUMENTS

| | | | |
|---|---|---|---|
| EP | 343388 A2 * | 11/1989 | |
| WO | WO 90/09780 A1 | 9/1990 | |
| WO | WO 98/02457 A1 | 1/1998 | |
| WO | WO 01/22970 A1 | 4/2001 | |
| WO | WO 03/028759 A1 | 4/2003 | |
| WO | WO 03/074561 A1 | 9/2003 | |
| WO | WO 03/092618 A2 | 11/2003 | |
| WO | WO 2004/022003 A2 | 3/2004 | |
| WO | WO 04/074314 A2 | 9/2004 | |
| WO | WO 2005/094420 A2 | 10/2005 | |

OTHER PUBLICATIONS

Park et al. (2004) Antiallergic Activity of Disaccaride Isolated from *Sanguisorba officinalis*. Phythotherapy Research 18:658-66.*
Verma et al., Gene therapy-promises, problems and prospects. (1997) Nature. 389:239-242.*
Orkin et al., Report and Reccommendations of the Panel to assess the NIH invextment in Research on Gene Therapy (1998) 1-41.*
Marshall., Gene Therapy's Growing Pains (1995) Science 269:1050-1055.*
Kreiss et al. (1999) Plasmid DNA size does not affect the physiochemical properties of lipoplexes but modulates gene transfer efficiency. Nucleic Acids Research 27:3792-2798.*
Carroll et al. (1998) Construction and Characterization of a Triple-Recombinant Vaccinia Virus Enclosing B7-1, Interleukin 12, and a Model Tumor Antigen. J. Nat. Canc. Inst. 90:1881-1887.*
Genbank Accesion No. B38957 (Jan. 12, 2000) pp. 1-2.*
O'Donnell (1999) J. Immunol. 163:4246-4252.*
Jong et al. (1997) J. Imuunol. 159:786-793.*
Nakahira (2002) J. Imuunol. 168:1146-1153.*
Adachi et al. (1999) J. Imuunol. 163:4367-4374.*
Scheerllinck, JPY. Vaccine 19:2647-2656, 2001.*
van Druen Littel-van den Hurk, S et al. Immunol Rev 199:113-125, 2004.*
Gautam, A et al. AM J Respir Med 1(1):35-46, 2002.*
Yang, X. Radiology 228:36-49, 2003.*
Kai, E, and T. Ochiya Pharm Res 21(5):838-843, 2004.*
Kumar, M. et al. "Chitosan IFN-γ -pDNA Nanoparticle (CIN) therapy for allergic asthma" Genetic Vaccines and Therapy, Oct. 2003, 1(1):3.
Barnes, P.J. "Cytokine-directed therapies for asthma" *J. Allergy Clin. Immunol.*, 2001, 108:S72-76.
Behera, A.K. et al. "Adenovirus-mediated interferon γ gene therapy for allergic asthma: involvement of interleukin 12 and STAT4 signaling" *Human Gene Therapy*, 2002, 13:1697-1709.

(Continued)

*Primary Examiner*—Deborah Crouch
*Assistant Examiner*—Marcia S Noble
(74) *Attorney, Agent, or Firm*—Saliwanchik, Lloyd & Saliwanchik

(57) ABSTRACT

The present invention pertains to methods and pharmaceutical compositions for modulating an immune response. The method of the present invention involves administration of an effective amount of nucleic acid molecules encoding interleukin-12 (IL-12), interferon-gamma (IFN-γ), or a combination thereof, to a patient in need of such treatment. The pharmaceutical compositions of the invention contain nucleic acid molecules encoding IL-12 and/or IFN-γ and an operably-linked promoter sequence. In another aspect, the present invention concerns expression vectors containing a nucleotide sequence encoding IL-12 and IFN-γ, and an operably-linked promoter sequence. In another aspect, the present invention concerns cells generally modified with a nucleotide sequence encoding IL-12 and IFN-γ.

31 Claims, 5 Drawing Sheets

OTHER PUBLICATIONS

Boraschi, D. et al., "Interferons inhibit $LTC_4$ production in murine macrophages" *J. Immunol.*, 1987, 138:4341-4346.

Byrnes, A.A. et al. "Type 1 interferons and IL-12: convergence and cross-regulation among mediators of cellular immunity" *Eur. J. Immunol.*, 2001, 31:2026-2034.

Chen, Q. et al. "Development of Th-1-type immune responses requires the type I cytokine receptor TCCR" *Nature*, 2000, 407:916-920.

Cohen, J. "IL-12 deaths: explanation and a puzzle" *Science*, 1995, 270:908.

Daines, M.O. and Hershey, G. "A novel mechanism by which interferon-γ can regulate interleukin (IL-13) responses" *J. Biol. Chem.*, 2002, 277 (12):10387-10393.

Deng, J.C. et al. "Transient transgenic expression of gamma interferon promotes *Legionella pneumophila* clearance in immunocompetent hosts" *Infection and Immunity*, 2001, 69(10):6382-6390.

Ford, J.G. et al. "IL-13 and IFN-γ: interactions in lung inflammation" *J. Immunol.*, 2001, 167:1769-1777.

Gavett, S.H. et al. "Interleukin 12 inhibits antigen-induced airway hyperresponsiveness, inflammation, and Th2 cytokine expression in mice" *J. Exp. Med.*, 1995, 182:1527-1536.

Gurujeyalakshmi, G. and Giri, S.N. "Molecular mechanisms of antifibrotic effect of interferon gamma in bleomycin-mouse model of lung fibrosis: downregulation of TGF-β and procollagen I and III gene expression" *Exp. Lung Res.*, 1995, 21:791-808.

Hansen, G. et al. "Allergen-specific Th1 cells fail to counterbalance Th2 cell-induced airway hyperreactivity but cause severe airway inflammation" *J. Clin. Invest.* 1999, 103:175-183.

Hansen, G. et al. CD4+ T helper cells engineered to produce latent TGF-β1 reverse allergen-induced airway hyperreactivity and inflammation *J. Clin. Invest.*, 2000, 105:61-70.

Hasbold, J. et al. "Integrating signals from IFN-γ and IL-4 by B cells: positive and negative effects on CD40 ligand-induced proliferation, survival, and division-linked isotype switching to IgG1, IgE, and IgG2a" *J. Immunol.*, 1999, 163:4175-4181.

Hasko, G. and Szabo, C. "IL-12 as therapeutic target for pharmacological modulation in immune-mediated and inflammatory diseases: regulation of T helper 1/T helper 2 responses" *Brit. J. Pharm.*, 1999, 127:1295-1304.

He, T-C. et al., "A simplified system for generating recombinant adenoviruses" *Proc. Natl. Acad. Sci.* USA, 1998, 95:2509-2514.

Kaplan, M.H. et al., "Impaired IL-12 responses and enhanced development of Th2 cells in Stat4-deficient mice" *Nature*, 1996, 382:174-177.

Kaplan, M.H. et al. "A signal transducer and activator of transcription (Stat)4-independent pathway for the development of T helper type 1 cells" *J. Exp. Med.*, 1998, 188(6):1191-1196.

Kirkwood, J.M. et al. "Interferon Alfa-2b adjuvant therapy of high-risk resected cutaneous melanoma: The Eastern Cooperative Oncology Group trial EST 1684" *J. Clin. Oncology*, 1996, 14(1):7-17.

Kitagawa, M. et al. "Interferon-γ enhances interleukin 12 production in rheumatoid synovial cells via CD40-CD154 dependent and independent pathways", J. Rheumatology, 2001, 28:1764-1771.

Kumar, M. et al. "Intranasal IFN-γ gene transfer protects BALB/c mice against respiratory syncytial virus infection" *Vaccine*, 2000, 18:558-567.

Kumar, M. et al. "IF-γ and IL-12 plasmid DNAs as vaccine adjuvant in a murine model of grass allergy" *J. Allergy Clin. Immunol.*, 2001, 108:402-408.

Lack, G. et al. "Nebulized but not parenteral IFN-γ decreases IgE production and normalizes airways function in a murine model of allergen sensitization" *J. Immunol.*, 1994, 152:2546-2554.

Li, X-M. et al. "Mucosal IFN-γ gene transfer inhibits pulmonary allergic responses in mice" *J. Immunol.*, 1996, 157:3216-3219.

Lighvani, A.A. et al. "T-bet is rapidly induced by interferon-γ in lymphoid and myeloid cells" *PNAS*, 2001, 98(26): 15137-15142.

Mastuse, H. et al. "Recurrent respiratory syncytial virus infections in allergen-sensitized mice lead to persistent airwa inflammation and hyperresponsiveness" *J. Immunol.*, 2000, 164:6583-6592.

Minshall, E.M. et al. "Eosinophil-associated TGF-1 mRNA expression and airways fibrosis in bronchial asthma" *Am. J. Respir. Cell Mol. Biol.*, 1997, 17:326-333.

Morrison, D.F. and Murtaugh, M.P. "Adenovirus-mediated expression of interleukin-1 receptor antagonist in swine cells in vitro and in vivo" *Veterinary Immunol. and Immunopathology*, 2001, 78:71-81.

Mosmann, T.R. and Coffman, R.L. "TH1 and TH2 cells: different patterns of lymphokine secretion lead to different functional properties" *Ann. Rev. Immunol.*, 1989, 7:145-173.

Mullen, A.C. et al. "Role of T-bet in commitment of $T_H1$ cells before IL-12-dependent selection" *Science*, 2001, 292:1907-1909.

O'Garra, A. and Arai, N. "The molecular basis of T helper 1 and T helper 2 cell differentiation" *Cell Biol.*, 2000, 10:542-550.

Oppmann, B. et al. "Novel p19 protein engages IL-12p40 to form a cytokine, IL-23, with biological activities similar as well as distinct from IL-12" *Immunity*, 2000, 13:715-725.

Pierkes, M. et al. "Decreases release of histamine and sulfidoleukotrienes by human peripheral blood leukocytes after wasp venom immunotherapy is partially due to induction of IL-10 and IFN-γ production of T cells" *J. Allergy Clin. Immunol.*, 1999, 103:326-332.

Randolph, D.A. et al. "Modulation of airway inflammation by passive transfer of allergen-specific Th1 and Th2 cells in a mouse model of asthma" *J. Immunol.*, 1999, 162:2375-2383.

Robinson, D.S. et al. "Predominant TH2-like bronchoalveolar T-lymphocyte population in atopic asthma" *N. Engl. J. Med.*, 1992, 326:298-304.

Rudick, R.A. et al. "Management of multiple sclerosis" *J. Engl. J. Med.*, 1997, 337(22):1604-1611.

Schwarze, J. et al. "Local treatment with IL-12 is an effective inhibitor of airway hyperresponsiveness and lung eosinophilia after airway challenge in sensitized mice" *J. Allergy Clin. Immunol.*, 1998, 102:86-93.

Stampfli, M.R., et al. "GM-CSF transgene expression in the airway allows aerosolized ovalbumin to induce allergic sensitization in mice" *J. Clin. Invest.*, 1998, 102:1704-1714.

Stirling, R.G. and Chung, K.F. "New Immunological approaches and cytokine targets in asthma and allergy" Eur Respir. J., 2000, 16:1158-1174.

Sur, S. et al. "Mucosal IL-12 inhibits airway reactivity to methacholine and respiratory failure in murine asthma" *Exp. Lung Res.*, 2000, 26:477-489.

Tang, C. et al. "Th type 1-stimulating activity of lung macrophages inhibits Th2-mediated allergic airway inflammation by an IFN-γ-dependent mechanism" *J. Immunol.* 2001, 166:1471-1481.

Thierfelder, W.E. et al. "Requirement for Stat4 in interleukin-12-mediated responses of natural killer and T cells" *Nature*, 1996, 382:171-174.

Thivierge, M. et al. "IL-13 and IL-4 up-regulated cysteinyl leukotriene 1 receptor expression in human monocytes and macrophages" *J. Immunol.*, 2001, 167:2855-2860.

Trinchieri, G. "Interleukin-12: a cytokine produced by antigen-presenting cells with immunoregulatory functions in the generation of T-helper cells type 1 and cytotoxic lymphocytes" *Blood*, 1994, 84(12):4008-4027.

Umestu, D.T. and Dekruyff, R.H. "TH1 and TH2 CD4* cells in human allergic diseases" *J. Allergy Clin. Immunol.* 1997, 100(1):1-6.

Walter, D.M et al. "IL-18 gene transfer by adenovirus prevents the development of and reverses established allergen-induced airway hyperractivity" *J. Immunol.*, 2001, 166:6392-6398.

Wang, I-M. et al. "An IFN-γ-inducible transcription factor, IFN consensus sequence binding protein (ICSBP), stimulates IL-12 p40 expression in macrophages" *J. Immunol.*, 2000, 165:271-279.

Zabner, J. et al. "Repeat administration of an adenovirus vector encoding cystic fibrosis transmembrane conductance regulator to the nasal epithelium of patients with cystic fibrosis" *J. Clin. Invest.*, 1996, 97:1504-1511.

Kumar, M. et al. "IFN-γ and IL-12 plasmid DNAs as vaccine adjuvant in a murine model of grass allergy" *J. Allergy Clin Immunol.*, Sep. 2001, 108:402-408.

Nonaka, M. et al. "Induction of eotaxin production by interleukin-4, interleukin-13 and lipopolysaccharide by nasal fibroblasts" *Clin. Exp. Allergy.* 2004, 34:804-811.

Upton, C. et al. "Enclođing of a homolog of the IFN-γ receptor by myxoma virus" *Science*, 1992, 258:1369-1372.

Vandenbroeck, K. et al. "The conserved helix C region in the superfamily of interferon-γ/interleukin-10-related cytokines corresponds to a high—affinity binding site for the HSP70 chaperone DnaK" *J. Biol. Chem.*, 2002, 277:25668-25676.

Zhu, Z. et al. "Acidic Mammalian chitinase in asthmatic Th2 inflammation and IL-13 pathway activation" *Science*, 2004, 304:1678-1682.

"Immunocytokines —Local Stimulation of the Immune System", 2002, www.merck.at/produkte/immunozytokine.pdf.

Stallmach, A. et al. "An Interleukin 12 p40-IgG2b Fusion Protein Abrogates T Cell Mediated Inflammation: Anti-Inflammatory Activity in Chron's Disease and Experimental Colitis In Vivo", *Gut.*, 2004, pp. 339-345, Vol. 53.

U.S. Appl. No. 10/526,584, filed Mar. 3, 2005, Mohapatra.

U.S. Appl. No. 10/544,145, filed Aug. 2, 2005, Mohapatra.

Antoniou, K.M. et al. "Interferons and their application in the diseases of the lung" *Chest*, 2003, 123:209-216.

Behera, A.K. et al. "2-5' oligoadenylate synthetase plays a critical role in interferon-y inhibition of respiraroy syncytial virus infection of human epithelial cells" *J. Biol: Chem*, 2002, 277(28):25601-25608.

Cevc, G. et al. "Ultraflexible vesicles, transfersomes, have an extremely low pore penetration resistance and transport therapeutic amounts of insulin across the intact mamalian skin" *Biochim. Biophys, Acta*, 1998, 1368:201-215.

Collins, P.L. et al. "Production of infectious human respiratory syncytial virus from cloned cDNA confirms an essential role for the transcription elongation factor from the 5' proximal open reading frame of the M2 mRNA in a gene expression and provides a capability for vaccine development" *PNAS USA*, 1995, 92:11563-11567.

Connors, M. et al. "Respiratory syncytical virus (RSV) F, G. M2 (22K), and N proteins each induce resistance to RSV challenge, but resistance induced by M2 and N proteins is relatively short-lived" *J. Virology*, 1991, 65:1634-1637.

Domachowske, J. and Rosenberg, H. "Respiratory syncytial virus infection: Immune response, immunopathogenesis, and treatment" *Clin. Microbiol. Rev.*, 1999, 12:298-309.

Dow, S. et al. "Systemic and local interferon γ gene delivery to the lungs for treatment of allergen-induced airway hyperresponsiveness in mice" *Human Gene Therapy*, 1999, 10:1905-1914.

Foldvari, M. and Moreland, A. "Clinical observations with topical liposome-encapsulated interferon alpha for the treatment of genital papillomavirus infections" *J. Liposome Res.*, 1997, 7:115-126.

Foldvari, M. et al. "Liposome encapsulated prostaglandin E1 in erectile dysfunction: Correlation between in vitro delivery through foreskin and efficacy in patients" *Urology*, 1998, 52(5):838-843.

Goeddel, D. et al. "The structure of eight distinct cloned human leukocyte interferon cDNAs" *Nature*, 1981, 290:20-26.

Gutterman, J.U "Cytokine therapeutics: Lessons from interferon a" *Proc. Natl. Acad. Sci. USA*, 1994, 91:1198-1205.

Hellermann, G.R. and Mohapatra, S.S. "Genetic therapy: on the brink of a new future" *Gen Vacc & Ther*, 2003, 1:1.

Henco, K. et al. "Structural Relationship of human interferon alpha genes and pseudogenes" *J. Mol. Biol.*, 1985, 185227-260.

Hofstra, C. et al., "Differential effects of endogenous and exogenous interferon-γ on immunoglobulin E, cellular infiltration, and airway respnsiveness in a murine model of allergic asthma" *Am. J. Respir. Cell Mol. Biol.*, 1998, 19:826-835.

HSU, S-C. et al. "Synergistic effect of immunization with a peptide cocktail inducing antibody, helper and cytotoxic T-cell responses on protection against respiratory syncytial virus" *J. Gen. Virology*, 1999, 80:1401-1405.

Huang, T-J. et al. "Allergen-specific Th1 cells counteract efferent Th2 cell-dependent bronchial hyperresponsiveness and eosinophilic inflammation partly via IFN-γ" *J. Immunol.*, 2001, 166:207-217.

Jameton, R. and Mohapatra, S.S. "IL-12 possibilities" *Science*, 1995, 269(5230):1298-1499.

Kumar, M. et al. "Role of mucosal IFN-γ gene transfer on allergic sensitization and RSV infection" *J. Allergy Clin. Immunol.*, 2002, 109:S4, abstract No. 78.

Kumar, M. et al. "Intranasal gene transfer by chitosan-DNA nanospheres protect BALB/c mice against acute respiratory syncytial virus infection" *Human Gene Ther.*, 2002, 13(12):1415-1425.

Lengyel, P. "Tumor-suppressor genes: News about the interferon connection" *Proc. Natl. Acad. Sci. USA*, 1993, 90:5893-5895.

Leong, K.W. et al. "DNA-polycation nanospheres as non-viral gene delivery vehicles" *J. Controlled Release*, 1998, 53:183-193.

LI, X. et al. "Protection against respiratory syncytial virus infection by DNA immunization" *J. Exp. Med.*, 1998, 188:681-688.

LI, X. et al. "Plasmid DNA encloding the respiratory syncytial virus G protein is a promising vaccine candidate" *Virology*, 2000, 269:54-65.

Mao, H-Q. et al. "Chitosan-DNA nanoparticles as gene carriers: synthesis, characterization and transfection efficiency" *J. Controlled Release*, 2001, 70(3):399-421.

Mohapatra, S.S. "Mucosal gene expression vaccine: a novel vaccine strategy for respiratory syncytial virus" *Pediatr. Infect. Dis. J.* 2003, 22(2 Suppl):S100-S104.

Montgomery, D. et al. "DNA vaccines" *Pharmacol. Ther.*, 1997, 74:195-205.

Murray, H.W. "Current and future clinical applications of interferon-gamma in host antimicrobial defense" *Intensive Care Med*, 1996, 22(Suppl 4):S456-S461.

Okubo, T. et al. "Administration of an IL-12-encoding DNA plasmid prevents the development of chronic graft-versus-host disease (GVH)" *J Immunol*, 1999, 162:403-4017.

Opdenakker, G. et al. "Interaction of Interferon with other cytokines" *Experientia*, 1989, 45:513-520.

Park, S-Y. et al. "IFN-y enhances Trail-induced apoptosis through IRF-1" *Eur. J. Biochem.*, 2004, 271(21):4222-4228.

Pizzoferrato, F. et al. "Ectopic expression of interferon regulatory factor-1 promotes human breast cancer cell death and results in reduced expression of survivin" *Cancer Res.*, 2004, 64(22):8381-8388.

Rener, X. et al. "Construction and identification of a recombinant adenovirus which expresses human interferon-γ" *Chinese J. Biotech.*, 1997, 13:1-8.

Robinson, M. and Kawabata, T. "Predictive assessment of respiratory sensitizing potential of proteins in mice" in Toxicology of Chemical Respiratory Hypersensitivity, Dearman and Kimber, Eds., 1997, pp. 135-150.

Roy, K. et al. "Oral gene delivery with chitosan-DNA nanoparticles generates immunologic protection in a murine model of peanut allergy" *Nat Med*, 1999, 5:387-391.

Sethi, S.K. et al. "Interferon-gamma (IFN-γ) down-regulates the rhinovirus-induced expression of intercellular adhesion molecule-1(ICAM-1) on human airway epithelial cells" *Clin. Exp. Immunol.*, 1997, 110:362-369.

Short, S.M. et al. "Percutaneous absorption of biologically-active interferon-gamma in a human skin graft-nude mouse model" *Pharm. Res.*, 1996, 13:1020-1027.

Simmons, C.P. et al. "Mucosal delivery of a respiratory syncytial virus CTL peptide with enterotoxin-based adjuvants elicits protective, immunopathogenic, and immunoregulatory antiviral CD8 T cell responses" *J. Immun.*, 2001, 166:1106-1113.

Streuli, M. et al. "At least three human type a interferons: Structure of α2" *Science*, 1980, 209:1343-1347.

Tang, Y-W. et al. "Determinants and kinetics of cytokine expression patterns in lungs of vaccinated mice challenged with respiratory syncytial virus" *Vaccine*, 1997, 15:597-602.

Wright, P. et al. "Evaluation of a live, cold-passaged, temperature-sensitive, respiratory syncytial virus vaccine candidate in infancy" *J. Infect. Dis.*, 2000, 182:1331-1342.

Wyatt, L.S. et al. "Priming and boosting immunity to respiratory syncytial virus b y recombinant replication-defective vaccinia virus MVA" *Vaccine*, 2000, 18:392-39.

Yoshida, M. et al. "Effect of interferon-α on allergic airway responses in interferon-γ-deficient mice" *Am J. Respir Crit Care Med.*, 2002, 166:451-456.

Zoon, K.c. "Human interferons: Structure and function" *Interferon*, 1987, 9:1-12.

Flotte, T.r. and Laube, B.L. "Gene therapy in cystic fibrosis" *Chest*, 2001, 120:124S-131S.

Gray, P.W. and Goeddel, D.V. "Cloning and expression of murine immune interferon cDNA" *Proc. Natl. Acad. Sci.* USA, 1983, 80:5842-5846.

Jooss, K. and Chirmule, N. "Immunity to adenovirus and adeno-associated viral vectors: implications for gene therapy" *Gene Therapy*, 2003, 10:955:963.

Kay, M.A. et al. "Viral vectors for gene therapy: the art of turning infectious agents into vehicles of therapeutics" *Nature Med.*, 2001, 7:33-40.

Mohapatra, S.M. et al., poster materials presented at the American Academy of Allergy Asthma in March 2002 and presented at the Immunology and American thoracic Society in May 2002.

Payne, L.G. et al. "Particle-mediated DNA vaccination of mice, monkeys and men: Looking beyond the dogma" *Curr Opin Mol Therap*, 2002, 4:459-466.

Somia, N. and Verma, I.M. "Gene therapy: Trials and tribulations" *Nature Rev.*, 2000, 1:91-99.

XIU, Q. et al. "Effect of intratracheally administered IL-12 recombinant adenovirus on ovalbumin induced bronchial hyresponsiveness in mouse model" *Chin J Tuberc Respir Dis*, 2001, 24:298-301.

Gill, D.r. et al. "The development of gene therapy for diseases of the lung" *Cell. Mol. Life Sci.*, 2004, 61:355-368.

Perricone, M.A. et al. "Aerosol and lobar administration of a recombinant adenovirus to individuals with cystic fibrosis. II. Transfection efficiency in airway epithelium" *Human Gene Therapy*, 2001, 12:1383-1394.

"Gene" from The American Heritage Dictionary of the English Language, 4th Ed. (online), 2000 (retrieved on Jun. 15, 2006). Retrieved from the Internet: [URL: http://dictionary.reference.com/browse/gene].

"Timolol Maleate"from RXList The Internet Drug Index (online), 2006 (retrieved on Jun. 15, 2006). Retrieved from the Internet: [URL:http://www.rxlist.com/cgi/generic3/timololgfs_wcp.htm].

"Respiratory tract" from Wikipedia (online). 2006 (retrieved on Jun. 15, 2006). Retrieved from the Internet: [URL:http://en.wikipedia.org/wiki/Respiratory_tract].

Dobson, J. "Gene therapy progress and pospects: magnetic nanoparticle-based gene delivery" *Gene Therapy*, 2006, 13:283-387.

Kinsey, B. et al. "Non-viral gene delivery to the lungs" *Current Gene Therapy*, 2005, 5:181-194.

Kumar, M.N.V.R. et al. "Nanoparticle-mediated gene delivery: state of the art" *Expert Opin. Biol. Ther.*, 2004, 4(8):1213-1224.

Pouton, C. and Seymour, L. "Key issues in non-viral gene delivery" *Adv. Drug Deliv. Rev.*, 2001, 46:187-203.

Read, M. et al. "Barriers to gene delivery using synthetic vectors" *Adv. in Genetics*, 2005, 53:19-46.

Grohmann, U., et al. "Positive Regulatory Role of IL-12 in Macrophages and Modulation by IFN-γ" *The Journal of Immunology*, 2001, 167:221-227.

* cited by examiner

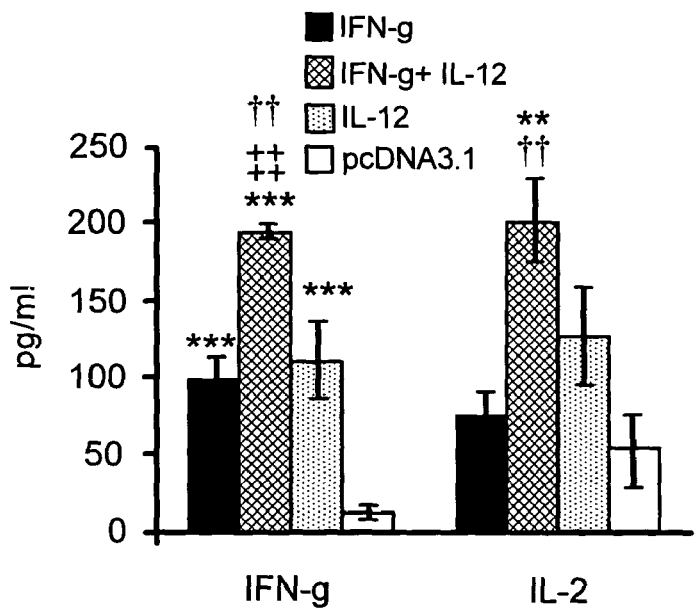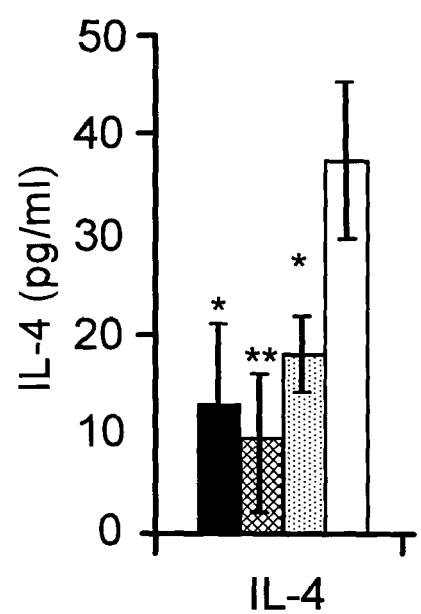
FIG. 3A  FIG. 3B
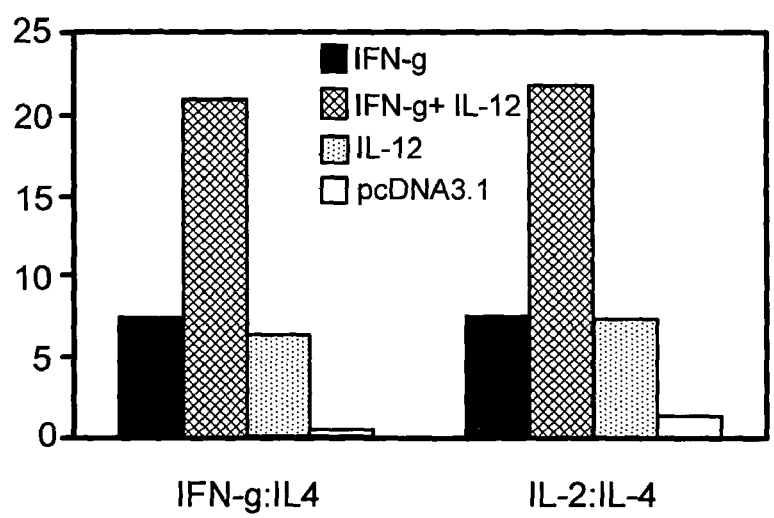
FIG. 3C

GENETIC ADJUVANTS FOR IMMUNOTHERAPY

CROSS-REFERENCE TO RELATED APPLICATION

The present application claims the benefit of priority of U.S. Provisional Application Ser. No. 60/319,523, filed Sep. 5, 2002, which is hereby incorporated by reference herein in its entirety, including any figures, tables, nucleic acid sequences, amino acid sequences, or drawings.

BACKGROUND OF INVENTION

The effectiveness of allergen immunotherapy (AIT) is often compromised by the use of high doses of allergens for treatment, which can lead to severe systemic reactions and the inconvenience and discomfort of frequent dosing (Kemp, S. F., *Immunol Allergy Clin North Am*, 2000, 20:571). It has been suggested that the utilization of an adjuvant in conjunction with an allergen vaccine might enhance both the safety and the effectiveness of AIT (Mohapatra, S. S. and San Juan, H. *Immunol Allergy Clin North Am*, 2000, 20:625-642). Two approaches are under investigation. The first is coimmunization with a mixture of antigen(s) and bacterial DNA or immunostimulatory oligodeoxynucleotides (ODNs), which contain CpG motifs (Horner, A. A. et al., *J. Allergy Clin Immunol*, 2000, 106:349-356) and elicit a protective $T_H1$ response (Roman, M. et al., *Nat Med*, 1997, 3:849-854). The potential of CpG-containing ODNs as adjuvants in AIT is under intense investigation; however, it has been reported that the immunostimulatory activity of these ODNs might be blocked by certain non-CpG motifs (Krieg, A. M. et al., *Proc Natl Acad Sci USA*, 1998, 95:12631-12636; Hacker, H. et al., *EMBO J*, 1998, 17:6230-6240). In addition, these ODNs might not suppress established allergic responses (Peng, Z. et al., *Int Immunol*, 2001, 13:3-11). In a second approach, the potential of plasmid DNA (pDNA)-encoding cytokine(s) as genetic adjuvants has been examined, with varying levels of success, for modulating the immune response stimulated by administered antigen vaccines (Pasquini, S. et al., *Immunol Cell Biol*, 1997, 75:397-401).

Cytokines interferon-γ (IFN-γ) and interleukin-12 (IL-12) are known to mediate T-cell differentiation toward a $T_H1$-like phenotype (Boehm, U. et al., *Annu Rev Immunol*, 1997, 15:749-795). Despite numerous studies in which pure or recombinant IFN-γ and IL-12 were used, their in vivo use has been limited by the short half-life of these molecules and the associated severe adverse effects (Mohapatra, S. S., *Science*, 1995, 269:1499). Mucosal IFN-γ gene transfer has earlier been shown to inhibit both antigen- and $T_H2$ cell-induced pulmonary eosinophilia and airway hyper-reactivity (Li, X. M. et al., *J. Immunol.*, 1996, 157:3116-3219). Vaccinia virus-mediated IL-12 gene transfer to the mouse airway abrogated airway eosinophilia and IgE synthesis (Hogan, S. P. et al., *Eur. J. Immunol.*, 1998, 28:413-423). However, the direct effects of these cytokine plasmids as genetic adjuvants in the allergen vaccines used for AIT have not been addressed.

In a previous study, a combination of allergen and IFN-γ effectively redirected allergen-specific T-cell cytokine production toward elevated IFN-γ production in human PBMC cultures (Parronchi, P. et al., *Eur J Immunol*, 1996, 26:697-703). In a murine model of Kentucky blue grass (KBG) allergy, parenteral administration of 1 mg of recombinant allergen induced effective immune deviation (Cao, Y. et al., *Immunology*, 1997, 90:46-51). Cytokine gene transfer studies have been carried out (Li, X. M. et al., *J. Immunol.*, 1996, 157:3116-3219; Hogan, S. P. et al., *Eur. J. Immunol.*, 1998, 28:413-423).

It would be advantageous to have the capability to mediate T-cell differentiation toward a $T_H1$-like phenotype using IFN-γ and/or IL-12, thereby enhancing the efficacy of allergen vaccines, without limitation by the short half-life of these molecules and the associated severe adverse effects.

BRIEF SUMMARY

The present invention pertains to methods and pharmaceutical compositions for modulating an immune response. The method of the present invention involves administration of an effective amount of nucleic acid molecules encoding interleukin-12 (IL-12), interferon-gamma (IFN-γ), or a combination thereof, to a patient in need of such treatment. In one embodiment, the nucleic acid molecules encoding IL-12 and/or IFN-γ are co-administered with an antigen.

The present invention further concerns pharmaceutical compositions comprising a nucleic acid sequence encoding IL-12 and/or IFN-γ and a pharmaceutically acceptable carrier. Preferably, the composition contains a nucleic acid sequence encoding both IL-12 and IFN-γ, and a pharmaceutically acceptable carrier. Optionally, in addition to a nucleic acid sequence encoding IL-12 and/or IFN-γ, the pharmaceutical composition of the present invention contains an antigen.

In another aspect, the present invention concerns expression vectors containing a nucleotide sequence encoding IL-12 and IFN-γ, and operably-linked promoter sequence. In another aspect, the present invention concerns cells genetically modified with a nucleotide sequence encoding IL-12 and IFN-γ.

BRIEF DESCRIPTION OF DRAWINGS

In FIG. 1E, total RNA was isolated from the muscle, and RT-PCR was performed for IFN-γ and IL-12 p40 subunit. Mice vaccinated with pIFN-γ and pIL-12 showed IFN-γ (panel 1, lane 2) and IL-12 p40-specific mRNA amplification (panel 1, lane 4). No amplification was observed in the mice vaccinated with control empty vector (panel 1, lanes 1 and 3), β-actin was used as internal control (lower panel).

FIGS. 3A-3C show analysis of cytokine production and dominant cytokine pattern following cytokine-encoding DNA vaccination. FIGS. 3A and 3B show analysis of cytokine production. Mice (n=6) were vaccinated as described in the Methods section. On day 7 after KBG and alum immunization, their spleens were cultured in vitro for 48 hours in the presence of KBG allergen and cytokines were measured by ELISA. Bars represent the means±SDs. *P<0.05; P<0.01; *P<0.001 in comparison with pcDNA3.1 group. †P<0.05; ††P<0.01; †††P<0.001 in comparison with pIFN-γ (IFN-g) group. ‡P<0.05; ‡‡P<0.01; ‡‡‡P<0.001 in comparison with pIL-12 (IL-12) group. FIG. 3C shows analysis of the dominant cytokine pattern after cytokine DNA vaccination. Dominant cytokine pattern was determined from the IFN-γ/IL-4 and IL-2/IL-4 ratios. Bars represent means.

FIG. 5B: pIFN-γ, FIG. 5C: pIL-12; FIG. 5D: pIFN-γ+pIL-12). Arrows indicated cellular infiltration. a, airway; v, vessel.

BRIEF DESCRIPTION OF SEQUENCES

Figure 1A:
FIGS. 1A-1E show expression of murine IFN-γ and IL-12 p40 subunit in the mouse muscle. Mice were vaccinated as described in the Methods section. Seven days after the last DNA injection, expression for IFN-γ and IL-12 p40 subunit was checked by immunohistochemistry (FIG. 1A-1D) and RT-PCR (FIG. 1E). Mice vaccinated with pIFN-γ (FIG. 1A) and pIL-12 (FIG. 1C) showed expression of IFN-γ and IL-12 p40 subunits, respectively, as indicated by positive staining (arrows). Mice vaccinated with control empty vector did not show expression for IFN-γ (FIG. 1B) and IL-12 p40 (FIG. 1D).

SEQ ID NO:1 is a forward primer for the murine IL-12 p40 subunit.

SEQ ID NO:2 is a reverse primer for the murine IL-12 p40 subunit.

SEQ ID NO:3 is a forward primer to generate the plasmid pc40.

SEQ ID NO:4 is a reverse primer to generate the plasmid pc40.

SEQ ID NO:5 is a forward primer for murine IL-12 p35 subunit.

SEQ ID NO:6 is a reverse primer for murine IL-12 p35 subunit.

SEQ ID NO:7 is a nucleotide sequence encoding the human IL-12 p35 subunit.

SEQ ID NO:8 is the amino acid sequence of the human IL-12 p35 subunit.

SEQ ID NO:9 is the nucleotide sequence of the human IL-12 p40 subunit.

SEQ ID NO:10 is the amino acid sequence of the human IL-12 p40 subunit.

SEQ ID NO:11 is the nucleotide sequence encoding human IFN-γ.

SEQ ID NO:12 is the amino acid sequence of human IFN-γ.

DETAILED DISCLOSURE

The present invention pertains to adjuvantation using nucleic acid molecules encoding IL-12, IFN-γ, or both IL-12 and IFN-γ. In one embodiment, the nucleic acid molecules encoding IL-12 and/or IFN-γ are co-administered with an antigen of the pathogen in order to modulate an immune response to a pathogen (one or more) in a patient (human or non-human mammal). Preferably, effective amounts of nucleic acid sequences encoding both IL-12 and IFN-γ are administered simultaneously or sequentially to a patient in need of such treatment. More preferably, effective amounts of nucleic acid sequences encoding both IL-12 and IFN-γ are administered simultaneously or sequentially to a patient, and an antigen is administered simultaneously or sequentially to the patient.

As described herein, the "immune response" modulated in the patient can be, for example, a cytokine immune response and/or a humoral immune response (e.g., antigen-specific). As used herein, the term "modulate", and grammatical variations thereof, is intended to mean strengthening (i.e., augmenting) or weakening (i.e., lessening, inhibiting) of an immune response within a patient. In one embodiment, the immune response of the patient is modulated such that production of IgE antibodies is inhibited. In further embodiments, the cytokine profiles of the patient's cells are altered to produce more $T_H1$-like cytokines (e.g., interleukin-2 (IL-2) and IFN-γ) and less $T_H2$-like cytokines ((interleukin-4) IL-4). The altered cytokine profile is more apparent in patients administered nucleic acid sequences encoding both IL-12 and IFN-γ. Depending upon the particular antigen that the patient is administered or otherwise exposed to (e.g., an allergen), the nucleic acid sequences encoding IL-12 and/or IFN-γ may inhibit or prevent airway hyper-responsiveness and inflammation.

Administration of nucleic acid molecules encoding IL-12 and/or IFN-γ, or biologically active fragments or homologs thereof, according to the subject invention, may be used to modulate the immune response in order to prevent or treat immune-related or inflammatory-related conditions such as, but not limited to, allergies, allergic rhinitis, atopic dermatitis, asthma, allergic sinusitis, pulmonary fibrosis, and cancer.

In other embodiments, the nucleic acid molecules used in the methods, vectors, cells, and compositions of the present invention encode IL-12-like molecules and/or IFN-γ-like molecules. As used herein, the terms "IL-12-like molecule" and "IFN-γ-like molecule" refers to polypeptides exhibiting IL-12-like activity and IFN-γ-like activity, respectively, when the nucleic acid molecule encoding the polypeptide is expressed, as can be determined in vitro or in vivo. For purposes of the subject invention, IL-12-like activity and IFN-γ-like activity refer to those polypeptides having one or more of the functions of the native IL-12 or IFN-γ cytokine, such as the capability to alter the cytokine profile of a patient's cells to produce more $T_H1$-like cytokines (e.g., interleukin-2 (IL-2) and IFN-γ) and less $T_H2$-like cytokines ((interleukin-4 (IL-4)). An example of an IL-12-like molecule is interleukin-23 (IL-23). Examples of IFN-γ-like molecules are interferon-alpha (IFN-α) and interferon-beta (IFN-β), including biologically active fragments thereof.

Following administration, the efficacy of the cytokine-encoding nucleic acid sequences can be assessed by specific cytokine production or antibody production, for example. One of ordinary skill in the art can assess these parameters using conventional methods.

A used herein, the term "antigen" is intended to mean one or more immunostimulatory agents capable of being bound by a selective binding agent, such as an antibody, and additionally capable of being used in an animal to produce antibodies capable of binding to an epitope of that antigen. An antigen may have one or more epitopes. Antigens can be molecules or portions of molecules including, but not limited to, proteins or fragments thereof (e.g., proteolytic fragments), peptides (e.g., synthetic peptides, polypeptides), glycoproteins, carbohydrates (e.g., polysaccharides), lipids, glycolipids, hapten conjugates, recombinant nucleotides (e.g., recombinant DNA), whole organisms (killed or attenuated) or portions thereof, toxins and toxoids (e.g., tetanus, diphtheria, cholera) and/or organic molecules. Particular examples of antigens for use in the present invention include allergens, such as Kentucky blue grass (KBG) allergen.

The antigen can be obtained or derived from a variety of pathogens or organisms, such as bacteria (e.g., *bacillus*, Group B *streptococcus*, Bordetella, Listeria, *Bacillus anthracis, S. pneumoniae, N. meningiditis, H. influenza*), viruses (e.g., hepatitis, measles, poliovirus, human immunodeficiency virus, influenza virus, parainfluenza virus, respiratory syncytial virus), mycobacteria (*M. tuberculosis*), parasites (Leishmania, Schisotosomes, Tranpanosomes, toxoplasma, pneumocystis) and fungi (e.g., *Candida, Cryptococcus, Coccidiodes, Aspergillus*), against which an immune response is desired in a patient. The antigen of a pathogen can be obtained using skills known in the art. For example, the antigen can be isolated (purified, essentially pure) directly from the pathogen, derived using chemical synthesis, or obtained using recombinant methodology. In addition, the antigen can be obtained from commercial sources. A suitable antigen for use in the present invention can include at least one B and/or T cell epitope (e.g., T helper cell or cytolytic T cell epitope). Other suitable antigens useful in the compositions of the present invention can be determined by those of skill in the art.

The IL-12-encoding nucleic acid sequence and IFN-γ-encoding nucleic acid sequence can be within the same nucleic acid molecule or separate nucleic acid molecules. Furthermore, it will be understood that a nucleic acid sequence can be a multimer comprising repeating units of the IL-12-encoding nucleic acid sequence and/or IFN-γ-encoding nucleic acid sequence (i.e., homopolymers or heteropolymers) for enhanced expression of the IL-12 and/or IFN-γ coding sequences, or biologically active fragments or homologs thereof.

As used herein, the term "co-administer", and grammatical variations thereof, is intended to mean administration of agents (e.g., nucleic acids, antigens, etc.) simultaneously or sequentially.

The nucleic acid sequences encoding IL-12 and/or IFN-γ used in the methods, expression vectors, and pharmaceutical compositions of the present invention are preferably isolated. According to the present invention, an isolated nucleic acid molecule or nucleic acid sequence is a nucleic acid molecule or sequence that has been removed from its natural milieu. As such, "isolated" does not necessarily reflect the extent to which the nucleic acid molecule has been purified. An isolated nucleic acid molecule or sequence useful in the present composition can include DNA, RNA, or any derivatives of either DNA or RNA. An isolated nucleic acid molecule or sequence can be double stranded (i.e., containing both a coding strand and a complementary strand) or single stranded.

Although the phrase "nucleic acid molecule" primarily refers to the physical nucleic acid molecule and the phrase "nucleic acid sequence" primarily refers to the sequence of nucleotides on the nucleic acid molecule, the two phrases are used interchangeably herein. As used herein, a "coding" nucleic acid sequence refers to a nucleic acid sequence that encodes at least a portion of a peptide or protein (e.g., a portion of an open reading frame), and can more particularly refer to a nucleic acid sequence encoding a peptide or protein which, when operably-linked to a transcription control sequence (e.g., a promoter sequence), can express the peptide or protein. A translation initiation codon can be inserted as necessary, making methionine the first amino acid in the sequence. Optionally, the IL-12 and/or IFN-γ encoding nucleic acid sequences used in the subject invention include a sequence encoding a signal peptide upstream of the cytokine(s)-encoding sequence(s), thereby permitting secretion of the IL-12 and/or IFN-γ, or a biologically active fragment thereof, from a host cell.

The term "operably-linked" is used herein to refer to an arrangement of flanking sequences wherein the flanking sequences so described are configured or assembled so as to perform their usual function. Thus, a flanking sequence operably-linked to a coding sequence may be capable of effecting the replication, transcription and/or translation of the coding sequence. For example, a coding sequence is operably-linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence, and the promoter sequence can still be considered "operably-linked" to the coding sequence. Each nucleotide sequence coding for IL-12 or IFN-γ will typically have its own operably-linked promoter sequence.

The term "vector" is used to refer to any molecule (e.g., nucleic acid, plasmid, or virus) used to transfer coding information (e.g., nucleic acid sequence encoding IL-12 and/or IFN-γ) to a host cell. The term "expression vector" refers to a vector that is suitable for use in a host cell (e.g., patient's cell) and contains nucleic acid sequences which direct and/or control the expression of heterologous nucleic acid sequences. Expression includes, but is not limited to, processes such as transcription, translation, and RNA splicing, if introns are present. A great variety of expression vectors can be used to produce IL-12 and/or IFN-γ, or biologically active fragments thereof. IL-12 and/or IFN-γ-encoding nucleic acid sequences can be modified according to methods known in the art to provide optimal codon usage for expression in a particular expression system.

In another aspect, the present invention includes pharmaceutical compositions comprising a nucleic acid sequence encoding IL-12 and/or IFN-γ and a pharmaceutically acceptable carrier. Preferably, the composition contains a nucleic acid sequence encoding both IL-12 and IFN-γ, and a pharmaceutically acceptable carrier. The nucleic acid sequence encoding IL-12 and/or IFN-γ may be contained within an expression vector, such as a DNA plasmid or viral vector (e.g., retrovirus, modified herpes virus, herpes virus, adenovirus, adeno-associated virus, and the like). Where a combination of nucleic acid sequences encoding IL-12 and IFN-γ are to be administered to a patient, sequences may be contained within one vector (e.g., a DNA plasmid) or separate vectors (e.g., separate plasmids), or types of vectors. Optionally, the pharmaceutical composition of the present invention further includes an antigen.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton, Pa., Mack Publishing Company, 19$^{th}$ ed.) describes formulations which can be used in connection with the subject invention. Formulations suitable for parental administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question. The pharmaceutical composition can be adapted for various forms of administration. Administration can be continuous or at distinct intervals as can be determined by a person skilled in the art.

The administration of the IL-12 and/or IFN-γ-encoding nucleic acid sequences are administered and dosed in accordance with good medical practice, taking into account the clinical condition of the individual patient, the site and method of administration, scheduling of administration, patient age, sex, body weight, and other factors known to medical practitioners. The pharmaceutically "effective amount" for purposes herein is thus determined by such considerations as are known in the art. A therapeutically effective amount of IL-12 and/or IFN-γ-encoding nucleic acid molecules is that amount necessary to provide a therapeutically effective amount of the corresponding polypeptide(s), when expressed in vivo. The amount of IL-12 and/or IFN-γ must be effective to achieve a modulated immune response, including but not limited to total prevention of (e.g., protection against) pathogen infection and/or allergic response, and to improved survival rate or more rapid recovery, or improvement or elimination of symptoms associated with pathogen infection or allergic response, and other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration.

Mammalian species which benefit from the disclosed compositions and methods include, and are not limited to, apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. As used herein, the term "patient" is intended to include such human and non-human mammalian species. Nucleic acid molecules encoding IL-12 and/or IFN-γ, or biologically active fragments thereof, can be administered to patients of the same species or different species from which the nucleic acid molecules naturally exist, for example.

The nucleic acid sequences encoding IL-12 and/or IFN-γ (and pharmaceutical compositions containing them) can be administered to a patient by any route that results in modulated immune response. For example, the genetic material can be administered intravenously (I.V.), intramuscularly (I.M.), subcutaneously (S.C.), intradermally (I.D.), orally, intranasally, etc.

Examples of intranasal administration can be by means of a spray, drops, powder or gel and also described in U.S. Pat. No. 6,489,306, which is incorporated herein by reference in its entirety. One embodiment of the present invention is the administration of the invention as a nasal spray. Alternate embodiments include administration through any oral or mucosal routes, sublingual administration, and even eye drops. However, other means of drug administrations are well within the scope of the present invention.

The present invention also encompasses combination therapy. By combination therapy is meant that nucleic acid sequences encoding IL-12 and/or IFN-γ can be administered in combination with other biologically active agents, such as antigens, other immunomodulators or immunostimulatory molecules, such as interferons or interleukens, and antimicrobial agents, such as antibiotics, antifungal drugs, antiviral drugs, etc.

The present invention can be conjugated with chitosan or chitosan derivatives. For example, DNA chitosan nanospheres can be generated, as described by Roy, K. et al. (*Nat Med*, 1999, 5:387). Chitosan allows increased bioavailability of the nucleic acid sequences because of protection from degradation by serum nucleases in the matrix and thus has great potential as a mucosal gene delivery system. Chitosan also has many beneficial effects, including anticoagulant activity, wound-healing properties, and immunostimulatory activity, and is capable of modulating immunity of the mucosa and bronchus-associated lymphoid tissue. In one embodiment of the present invention, chitosan derived nanoparticles are used as adjuvants or conjugates.

IL-12 is a heterodimeric cytokine that has a molecular weight of 75 kDa and is composed of disulfide-bonded 40 kDa and 35 kDa subunits. As used herein, "interleukin-12" and "IL-12" refer to interleukin 12 protein, its individual subunits, multimers of its individual subunits, biologically active fragments of IL-12, and biologically active homologs of "interleukin-12" and "IL-12", such as mammalian homologs. As defined herein, biologically active fragments of IL-12 are fragments that, for example, modulate an immune response to an antigen in a patient who has been administered or otherwise exposed to the antigen. As also defined herein, biologically active fragments or homologs of "interleukin-12" and "IL-12" include modified IL-12 protein such that the resulting IL-12 product has immune response modulation activity similar to the IL-12 described herein (e.g., the ability to modulate an immune response to an antigen, when administered with the antigen, in a patient, relative to in vivo conditions in the absence of the cytokine or relative to administration of the antigen alone). Biologically active homologs or fragments of "interleukin-12" also include nucleic acid sequences (e.g., DNA, RNA) and portions thereof, which encode a protein or peptide having the IL-12 function or activity described herein (e.g., the ability to modulate an immune response to an antigen, when administered with the antigen, in a patient). In addition, the term includes a nucleotide sequence which, through the degeneracy of the genetic code, encodes a similar peptide gene product as IL-12 and has the IL-12 activity described herein. For example, a homolog of "interleukin-12" and "IL-12" includes a nucleotide sequence which contains a "silent" codon substitution (e.g., substitution of one codon encoding an amino acid for another codon encoding the same amino acid) or an amino acid sequence which contains a "silent" amino acid substitution (e.g., substitution of one acidic amino acid for another acidic amino acid).

An exemplified nucleotide sequence encodes the human IL-12 p35 subunit (Accession No: NM_000882, NCBI database, which is hereby incorporated by reference in its entirety):

1 tttcattttg ggccgagctg gaggcggcgg ggccgtcccg gaacggctgc ggccgggcac
61 cccgggagtt aatccgaaag cgccgcaagc cccgcgggcc ggccgcaccg cacgtgtcac
121 cgagaagctg atgtagagag agacacagaa ggagacagaa agcaagagac cagagtcccg
181 ggaaagtcct gccgcgcctc gggacaatta taaaaatgtg gcccctggg tcagcctccc
241 agccaccgcc ctcacctgcc gcggccacag gtctgcatcc agcggctcgc cctgtgtccc
301 tgcagtgccg gctcagcatg tgtccagcgc gcagcctcct ccttgtggct accctggtcc
361 tcctggacca cctcagtttg gccagaaacc tccccgtggc cactccagac caggaatgt
421 tcccatgcct tcaccactcc caaaacctgc tgagggccgt cagcaacatg ctccagaagg
481 ccagacaaac tctagaattt tacccttgca cttctgaaga gattgatcat gaagatatca
541 caaaagataa aaccagcaca gtggaggcct gtttaccatt ggaattaacc aagaatgaga
601 gttgcctaaa ttcagagag acctctttca taactaatgg gagttgcctg gcctccagaa
661 agacctcttt tatgatggcc ctgtcaatta gtagtattta tgaagacttg aagatgtacc
721 aggtggagtt caagaccatg aatgcaaagc ttctgatgga tcctaagagg cagatctttc
781 tagatcaaaa catgctggca gttattgatg agctgatgca ggccctgaat ttcaacagtg
841 agactgtgcc acaaaaatcc tcccttgaag aaccggattt ttataaaact aaaatcaagc
901 tctgcatact tcttcatgct ttcagaattc gggcagtgac tattgataga gtgatgagct
961 atctgaatgc ttcctaaaaa gcgaggtccc tccaaaccgt tgtcattttt ataaaacttt
1021 gaaatgagga aactttgata ggatgtggat taagaactag ggagggggaa agaaggatgg
1081 gactattaca tccacatgat acctctgatc aagtatttt gacatttact gtggataaat
1141 tgttttaag ttttactgaa tgaattgcta agaagggaaa atatccatcc tgaaggtgtt
1201 tttcattcac tttaatagaa gggcaaatat ttataagcta tttctgtacc aaagtgtttg
1261 tggaaacaaa catgtaagca taacttattt taaaatattt atttatataa cttgtaatc
1321 atgaaagcat ctgagctaac ttatatttat ttatgttata tttattaaat tatt-tatcaa
1381 gtgtatttga aaaatatttt taagtgttct aaaaataaaa gtattgaatt aaagtgaaaa
1441 aaaa (SEQ ID NO:7)

MWPPGSASQPPPSPAAATGLHPAARPVS-LQCRLSMCPARSLLLVATLVLLDHLSLAR NLPVAT-PDPGMFPCLHHSQNLLRAVSNMLQKAR-QTLEFYPCTSEEIDHEDITKDKTSTVEACLPLELTK-NESCLNSRETSFITNGSCLASRKTSFM-MALCLSSIYEDLKMYQVEFKTMNAKLLM-DPKRQIFLDQNMLAVIDELMQALN-FNSETVPQKSSLEEPDFYKTKLHAFRIRAVTIDRVM-SYLNAS (SEQ ID NO:8)

A further exemplified nucleotide sequence encodes the human IL-12 p40 subunit (Accession No: NM_002187, NCBI database, which is hereby incorporated by reference in its entirety):

1 ctgtttcagg gccattggac tctccgtcct gcccagagca agatgtgtca ccagcagttg
61 gtcatctctt ggttttccct ggttttctg gcatctcccc tcgtggccat atgggaactg
121 aagaaagatg tttatgtcgt agaattggat tggtatccgg atgcccctgg agaaatggtg
181 gtcctcacct gtgacacccc tgaagaagat ggtatcacct ggacctgga ccagagcagt
241 gaggtcttag gctctggcaa aacccctgacc atccaagtca aagagtttgg agatgctggc
301 cagtacacct gtcacaaagg aggcgaggtt ctaagccatt cgctcctgct gcttcacaaa
361 aaggaagatg gaatttggtc cactgatatt ttaaaggacc agaaagaacc caaaaataag
421 acctttctaa gatgcgaggc caagaattat tctggacgtt tcacctgctg gtggctgacg
481 acaatcagta ctgatttgac attcagtgtc aaaagcagca gaggctcttc tgacccccaa
541 ggggtgacgt gcggagctgc tacactctct gcagagagag tcagagggga caacaaggag
601 tatgagtact cagtggagtg ccaggaggac agtgcctgcc cagctgctga ggagagtctg
661 cccattgagg tcatggtgga tgccgttcac aagctcaagt atgaaaacta caccagcagc
721 ttcttcatca gggacatcat caaacctgac ccacccaaga acttgcagct gaagccatta
781 aagaattctc ggcaggtgga ggtcagctgg gagtaccctg acacctggag tactccacat
841 tcctacttct ccctgacatt ctgcgttcag gtccagggca agagcaagag agaaaagaaa
901 gatagagtct tcacggacaa gacctcagcc acggtcatct gccgcaaaaa tgccagcatt
961 agcgtgcggg cccaggaccg ctactatagc tcatcttgga gcgaatgggc atctgtgccc
1021 tgcagttagg ttctgatcca ggatgaaaat ttggaggaaa agtggaagat attaagcaaa
1081 atgtttaaag acacaacgga atagacccaa aaagataatt tctatctgat ttgctttaaa
1141 acgtttttt aggatcacaa tgatatcttt gctgtatttg tatagttaga tgctaaatgc
1201 tcattgaaac aatcagctaa tttatgtata gattttccag ctctcaagtt gccatgggcc
1261 ttcatgctat ttaaatattt aagtaattta tgtatttatt agtatattac tgttatt-taa
1321 cgtttgtctg ccaggatgta tggaatgttt catactctta tgacctgatc catcaggatc
1381 agtcccctatt atgcaaaatg tgaatttaat tttatttgta ctgacaactt ttcaagcaag
1441 gctgcaagta catcagtttt atgacaatca ggaagaatgc agtgttctga taccagtgcc
1501 atcatacact tgtgatggat gggaacgcaa gagatactta catggaaacc tgacaatgca
1561 aacctgttga gaagatccag gagaacaaga tgctagttcc catgtctgtg aagacttcct
1621 ggagatggtg ttgataaagc aatttagggc cacttacact tctaagcaag tttaatcttt 1681 ggatgcctga attttaaaag ggctagaaaa aaatgattga ccagcctggg aaacataaca 1741 agaccccgtc tctacaaaaa aaatttaaaa ttagccaggc gtggtggctc atgcttgtgg 1801 tcccagctgt tcaggaggat gaggcaggag gatctcttga gcccaggagg tcaaggctat 1861 ggtgagccgt gattgtgcca ctgcatacca gcctaggtga cagaatgaga ccctgtctca 1921 aaaaaaaaaa tgattgaaat taaaattcag ctttagcttc catggcagtc ctcaccccca 1981 cctctctaaa agacacagga ggatgacaca gaaacaccgt aagtgtctgg aaggcaaaaa 2041 gatcttaaga ttcaagagag aggacaagta gttatggcta aggacatgaa attgtcagaa 2101 tggcaggtgg cttcttaaca gccctgtgag aagcagacag atgcaaagaa aatctggaat 2161 cccttctca ttagcatgaa tgaacctgat acacaattat gaccagaaaa tatggctcca 2221 tgaaggtgct acttttaagt aatgtatgtg cgctctgtaa agtgattaca tttgtttcct 2281 gtttgtttat ttatttattt attttgcat tctgaggctg aactaataaa aactcttctt 2341 tgtaatc (SEQ ID NO:9)

MCHQQLVISWFSLVFLASPLVAI-
WELKKDVYVVELDWYPDAPGEMVVLTCDTPEED
GITWTLDQSSEVLGSGKTLTIQVKEF-
GDAGQYTCHKGGEVLSHSLLLLHKKEDGIWS
TDILKDQKEPKNKTFLRCEAKNYSGR-
FTCWWLTTISTDLTFSVKSSRGSSDPQGVTC
GAATLSAERVRGDNKEYEYSVEC-
QEDSACPAAEESLPIEVMVDAVHKLKYENYTSS
FFIRDIIKPDPPKNLQLKPLKN-
SRQVEVSWEYPDTWSTPHSYFSLT-
FCVQVQGKSKRE KKDRVFTDKTSATVICRKNA-
SISVRAQDRYYSSSWSEWASVPCS (SEQ ID NO:10)

IFN-γ is a 14-18 kDalton 143 amino acid glycosylated protein that is a potent multifunctional cytokine. As used herein, "interferon-gamma" and "IFN-γ" refer to IFN-γ protein, biologically active fragments of IFN-γ, and biologically active homologs of "interferon-gamma" and "IFN-γ", such as mammalian homologs. As defined herein, biologically active fragments of IFN-γ are fragments that, for example, modulate an immune response to an antigen in a patient who has been administered or otherwise exposed to the antigen. As also defined herein, biologically active fragments or homologs of "interferon-gamma" and "IFN-γ" include modified IFN-γ protein such that the resulting IFN-γ product has immune response modulating activity similar to the IFN-γ described herein (e.g., the ability to modulate an immune response to an antigen, when administered with the antigen, in a patient, relative to in vivo conditions in the absence of the cytokine or relative to administration of the antigen alone). Biologically active homologs or fragments of "interferon-gamma" also include nucleic acid sequences (e.g., DNA, RNA) and portions thereof, which encode a protein or peptide having the IFN-γ function or activity described herein (e.g., the ability to modulate an immune response to an antigen in a patient that has been administered or otherwise exposed to the antigen). In addition, the term includes a nucleotide sequence which through the degeneracy of the genetic code encodes a similar peptide gene product as IFN-γ and has the IFN-γ activity described herein. For example, a homolog of "interferon-gamma" and "IFN-γ" includes a nucleotide sequence which contains a "silent" codon substitution (e.g., substitution of one codon encoding an amino acid for another codon encoding the same amino acid) or an amino acid sequence which contains a "silent" amino acid substitution (e.g., substitution of one acidic amino acid for another acidic amino acid).

A further exemplified nucleotide sequence encodes human IFN-γ (Accession No. NM_000619), NCBI database, which is hereby incorporated by reference in its entirety):

1 cacattgttc tgatcatctg aagatcagct attagaagag aaagatcagt taagtccttt 61 ggacctgatc agcttgatac aagaactact gatttcaact tctttggctt aattctctcg 121 gaaacgatga aatatacaag ttatatcttg gcttttcagc tctgcatcgt tttgggttct 181 cttggctgtt actgccagga cccatatgta aaagaagcag aaaaccttaa gaaatatttt 241 aatgcaggtc attcagatgt agcggataat ggaactcttt tcttaggcat tttgaagaat 301 tggaaagagg agagtgacag aaaaataatg cagagccaaa ttgtctcctt ttacttcaaa 361 cttttaaaa acttaaaga tgaccagagc atccaaaaga gtgtggagac catcaaggaa 421 gacatgaatg tcaagttttt caatagcaac aaaaagaaac gagatgactt cgaaaagctg 481 actaattatt cggtaactga cttgaatgtc caacgcaaag caatacatga actcatccaa 541 gtgatggctg aactgtcgcc agcagctaaa acagggaagc gaaaaagagag tcagatgctg 601 tttcgaggtc gaagagcatc ccagtaatgg ttgtcctgcc tgcaatattt gaatttaaa 661 tctaaatcta tttattaata tttaacatta tttatatggg gaatatattt ttagactcat 721 caatcaaata agtatttata atagcaactt ttgtgtaatg aaaatgaata tctattaata 781 tatgtattat ttataattcc tatatcctgt gactgtctca cttaatcctt tgttttctga 841 ctaattaggc aaggctatgt gattacaagg ctttatctca ggggccaact aggcagccaa 901 cctaagcaag atcccatggg ttgtgtgttt atttcacttg atgataacat gaacactat 961 aagtgaagtg atactatcca gttactgccg gtttgaaaat atgcctgcaa tctgagccag 1021 tgctttaatg gcatgtcaga cagaacttga atgtgtcagg tgaccctgat gaaaacatag 1081 catctcagga gatttcatgc ctggtgcttc caaatattgt tgacaactgt gactgtaccc 1141 aaatggaaag taactcattt gttaaaatta tcaatatcta atatatatga ataaagtgta 1201 agttcacaac aaaaaaaaaa aaaaaaaaaa aaaaaaaaaa (SEQ ID NO: 11)

The corresponding amino acid sequence for human IFN-γ (Accession No. NP_000610), NCBI database, is hereby incorporated by reference in its entirety):

1 MKYTSYILAF QLCIVLGSLG CYCQDPYVKE AENLKKYFNA GHSDVADNGT LFLGILKNWK

61 EESDRKIMQS QIVSFYFKLF KNFKDDQSIQ KSVETIKEDM NVKFFNSNKK KRDDFEKLTN

121 YSVTDLNVQR KAIHELIQVM AELSPAAKTG KRKRSQMLFR GRRASQ (SEQ ID NO:12)

The nucleotide sequences encoding IL-12 and/or IFN-γ used in the subject invention include "homologous" or "modified" nucleotide sequences. Modified nucleic acid sequences will be understood to mean any nucleotide sequence obtained by mutagenesis according to techniques well known to persons skilled in the art, and exhibiting modifications in relation to the normal sequences. For example, mutations in the regulatory and/or promoter sequences for the expression of a polypeptide that result in a modification of the level of expression of a polypeptide according to the invention provide for a "modified nucleotide sequence". Likewise, substitutions, deletions, or additions of nucleic acids to the polynucleotides of the invention provide for "homologous" or "modified" nucleotide sequences. In various embodiments, "homologous" or "modified" nucleic acid sequences have substantially the same biological or serological activity as the native (naturally occurring) IL-12 and/or IFN-γ peptide. A "homologous" or "modified" nucleotide sequence will also be understood to mean a splice variant of the polynucleotides of the instant invention or any nucleotide sequence encoding a "modified polypeptide" as defined below.

A homologous nucleotide sequence, for the purposes of the present invention, encompasses a nucleotide sequence having a percentage identity with the bases of the nucleotide sequences of between at least (or at least about) 20.00% to 99.99% (inclusive). The aforementioned range of percent identity is to be taken as including, and providing written description and support for, any fractional percentage, in intervals of 0.01%, between 20.00% and 99.99%. These percentages are purely statistical and differences between two nucleic acid sequences can be distributed randomly and over the entire sequence length.

In various embodiments, homologous sequences exhibiting a percentage identity with the bases of the nucleotide sequences of the present invention can have 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity with the polynucleotide sequences of the instant invention. Homologous nucleic acid sequences and amino acid sequences include mammalian homologs of the human IL-12 and/or IFN-γ nucleic acid sequences and amino acid sequences, including homologs of biologically active fragments, such as biologically active subunits.

Both protein and nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman *Proc. Natl. Acad. Sci. USA,* 1988, 85(8):2444-2448; Altschul et al. *J. Mol. Biol.,* 1990, 215(3): 403-410; Thompson et al. *Nucleic Acids Res.,* 1994, 22(2): 4673-4680; Higgins et al. *Methods Enzymol.,* 1996, 266:383-402; Altschul et al. *J. Mol. Biol.,* 1990, 215(3):403-410; Altschul et al. *Nature Genetics,* 1993, 3:266-272).

Identity and similarity of related nucleic acid molecules and polypeptides can be readily calculated by known methods. Such methods include, but are not limited to, those described in Computational Molecular Biology, Lesk, A. M., ed., Oxford University Press, New York, 1988; York (1988); Biocomputing: Informatics and Genome Projects, Smith, D. W., ed., Academic Press, New York, 1993; York (1993); Computer Analysis of Sequence Data, Part 1, Griffin, A. M., and Griffin, H. G., eds., Humana Press, New Jersey, 1994; Jersey (1994); Sequence Analysis in Molecular Biology, von Heinje, G., Academic Press, 1987; Press (1987); Sequence Analysis Primer, Gribskov, M. and Devereux, J., eds., M. Stockton Press, New York, 1991; York (1991); and Carillo et al., SIAM J. Applied Math., 48:1073 (1988).

The methods, pharmaceutical compositions, and vectors of the present invention can utilize biologically active fragments of nucleic acid sequences encoding IL-12 and/or IFN-γ. Representative fragments of the polynucleotide sequences according to the invention will be understood to mean any polynucleotide fragment having at least 8 or 9 consecutive nucleotides, preferably at least 12 consecutive nucleotides, and still more preferably at least 15 or at least 20 consecutive nucleotides of the sequence from which it is derived. The upper limit for such fragments is the total number of nucleotides found in the full-length sequence (or, in certain embodiments, of the full length open reading frame (ORF) identified herein).

In other embodiments, fragments can comprise consecutive nucleotides of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, and up to one nucleotide less than the full-length IL-12 and/or IFN-γ coding sequences. In some embodiments, fragments comprise biologically active subunits of IL-12 and/or IFN-γ (e.g., p35 and/or p40 subunit of IL-12), or biologically active fragments of such subunits.

It is also well known in the art that restriction enzymes can be used to obtain biologically active fragments of the nucleic acid sequences, such as those encoding IL-12 and/or IFN-γ. For example, Bal31 exonuclease can be conveniently used for time-controlled limited digestion of DNA (commonly referred to as "erase-a-base" procedures). See, for example, Maniatis et al. [1982] *Molecular Cloning: A Laboratory Manual,* Cold Spring Harbor Laboratory, New York; Wei et al. [1983] *J. Biol. Chem.* 258:13006-13512.

The methods of the subject invention also contemplate the administration of cells that have been genetically modified to produce both IL-12 and IFN-γ, or biologically active fragments thereof. Such genetically modified cells can be administered alone or in combinations with different types of cells. Thus, genetically modified cells of the invention can be co-administered with other cells, which can include genetically modified cells or non-genetically modified cells. Genetically modified cells may serve to support the survival and function of the co-administered cells, for example.

The term "genetic modification" as used herein refers to the stable or transient alteration of the genotype of a cell of the subject invention by intentional introduction of exogenous nucleic acids by any means known in the art (including for example, direct transmission of a polynucleotide sequence from a cell or virus particle, transmission of infective virus particles, and transmission by any known polynucleotide-bearing substance) resulting in a permanent or temporary alteration of genotype. The nucleic acids may be synthetic, or naturally derived, and may contain genes, portions of genes, or other useful polynucleotides in addition to those encoding IL-12 and IFN-γ, or biologically active fragments thereof. A translation initiation codon can be inserted as necessary, making methionine the first amino acid in the sequence. The term "genetic modification" is not intended to include naturally occurring alterations such as that which occurs through natural viral activity, natural genetic recombination, or the like. The genetic modification may confer the ability to produce IL-12 and IFN-γ, or biologically active fragments thereof, wherein the cell did not previously have the capability, or the modification may increase the amount of IL-12 and IFN-γ produced by the cell, e.g., through increased expression.

Exogenous nucleic acids and/or vectors encoding IL-12 and/or IFN-γ, or biologically active fragments thereof, can be introduced into a cell by viral vectors (retrovirus, modified herpes virus, herpes virus, adenovirus, adeno-associated virus, and the like) or direct DNA transfection (lipofection, calcium phosphate transfection, DEAE-dextran, electroporation, and the like), microinjection, cationic lipid-mediated transfection, transduction, scrape loading, ballistic introduction and infection (see, for example, Sambrook et al. [1989] *Molecular Cloning: A Laboratory Manual*, 2$^{nd}$ Ed., Cold Spring Harbor Laboratory Press, Cold Spring Harbor, N.Y.).

Preferably, the exogenous nucleic acid sequence encoding IL-12 and/or IFN-γ, or biologically active fragments thereof, is operably linked to a promoter sequence that permits expression of the nucleic acid sequence in a desired tissue within the patient. The promoters can be inducible or tissue specific as necessary.

The genetically modified cell may be chosen from eukaryotic or prokaryotic systems, for example bacterial cells (Gram negative or Gram positive), yeast cells, animal cells, plant cells, and/or insect cells using baculovirus vectors. In some embodiments, the genetically modified cell for expression of the nucleic acid sequences encoding IL-12 and/or IFN-γ, or biologically active fragments thereof, are human or non-human mammal cells.

Standard molecular biology techniques known in the art and not specifically described were generally followed as in Sambrook et al., Molecular Cloning: A Laboratory Manual, Cold Spring Harbor Laboratory Press, New York (1989), and in Ausubel et al., Current Protocols in Molecular Biology, John Wiley and Sons, Baltimore, Md. (1989) and in Perbal, A Practical Guide to Molecular Cloning, John Wiley & Sons, New York (1988), and in Watson et al., Recombinant DNA, Scientific American Books, New York and in Birren et al. (eds) Genome Analysis: A Laboratory Manual Series, Vols. 1-4 Cold Spring Harbor Laboratory Press, New York (1998) and methodology as set forth in U.S. Pat. Nos. 4,666,828; 4,683,202; 4,801,531; 5,192,659; and 5,272,057; and incorporated herein by reference. Polymerase chain reaction (PCR) was carried out generally as in PCR Protocols: A Guide To Methods And Applications, Academic Press, San Diego, Calif. (1990). In situ (In-cell) PCR in combination with Flow Cytometry can be used for detection of cells containing specific DNA and mRNA sequences (Testoni et al., *Blood*, 1996, 87:3822).

MATERIALS AND METHODS

Animals. Female B6D2F1 mice, 6 to 8 weeks old, from Jackson Laboratory (Bar Harbor, Me.) were maintained in pathogen-free conditions at the animal center at the James A. Haley Veterans Hospital. All procedures were reviewed and approved by the committee on animal research at the James A. Haley VA Medical Center and the University of South Florida College of Medicine.

Vaccination protocol. Four groups of naive mice (n=12) were intramuscularly vaccinated 3 times at intervals of 2 days, each in its right quadriceps muscle, with 100 μg of pIFN-γ, 100 μg of pIL-12, or a mixture of pIL-12 and pIFN-γ (50 μg of each), along with subcutaneous injection of 50 μg per mouse of crude KBG extract given at the back of the animal. Control mice each received 100 μg of pcDNA3.1 plasmid and 50 μg of KBG allergen extract. Seven days after the last DNA and KBG vaccinations, control and experimental groups of mice were immunized intraperitoneally with 10 μg of KBG allergen and 1 mg of alum.

Construction of the pIL-12 and pIFN-γ plasmids. To clone murine IL-12, the IL-12 p40 subunit was amplified from a mouse cDNA library as an NheI-XhoI cassette through use of the following set of primers: forward primer 5'-dCCA GGC AGC TAG CAG CAA AGC AA-3' (SEQ ID NO:1) and reverse primer 5'-dTCC CTC GAG GCA TCC TAG GAT CGG AC-3' (SEQ ID NO:2). The amplified product was ligated to the mammalian expression vector pcDNA 3.1 (IN-VITROGEN, San Diego, Calif.) at the corresponding sites. The resulting plasmid, pcP40, was used as the template to amplify the p40 subunit and bovine growth hormone (BGH) poly A sequences derived from the pcDNA 3.1 vector as an HindIII-KpnI cassette and ligated to pcDNA 3.1 at the corresponding sites to generate the plasmid pc40. The following primers were used: 5'-dACC CAA GCT TGC TAG CAG CAA A-3' (SEQ ID NO:3) and 5'-dGAA GCC ATA GAG GGT ACC GCA TC-3' (SEQ ID NO:4). Through use of forward primer 5'-dTGC GGA TCC AGC ATG TGT CAA T-3' (SEQ ID NO:5) and reverse primer 5'-dGCA GAG GGC CTC GAG CTT TCA G-3' (SEQ ID NO:6), the p35 subunit of murine IL-12 was amplified as a BamHI-XhoI fragment and cloned into pcDNA3.1 to generate to pcP35 vector. With pcP35 used as a template, the cytomegalovirus (CMV) promoter and p35 subunit were as an EcoRI-EcoRV cassette and ligated to the corresponding site in the vector pc40. The resulting plasmid, pIL-12, had each of the 2 subunits of IL-12 under a separate CMV promoter and a BGH gene poly A sequence. Murine IFN-γ was cloned in pcDNA3.1; the construction of this plasmid has been described elsewhere (Kumar, M. et al., *Vaccine*, 1999, 18:558-567). Large-scale plasmid preparation was preformed through use of a QIAGEN kit (QIAGEN, Valencia, Calif.).

Immunohistochemistry. Groups of naive mice were vaccinated intramuscularly 3 times with 100 μg of pIFN-γ, pIL-12, or pcDNA3.1 control vector at intervals of 2 days each. Seven days after the last vaccination, the mice were killed and their right quadriceps muscles were removed and subjected to paraffin embedding, as described previously (Kumar, M. et al., *Vaccine*, 1999, 18:558-567). Immunostaining for IFN-γ and IL-12 was preformed through use of polyclonal antibodies (Santa Cruz Biotechnology, Santa Cruz, Calif.) against murine IFN-γ and the murine IL-12 p40 subunit, as described previously (Matsue, H. et al., *J. Immunol.*, 2000, 164:6583-6592).

Splenocyte culture and assay for cytokines. Seven days after the KBG immunization, one half of the animals in each group were killed and their spleens removed aseptically. Single-cell suspensions were cultured with 1 mg/mL KBG allergen for 48 hours. Supernatants were collected from the cultures, and the production of IFN-γ, IL-2, and IL-4 was determined by ELISA (R&D Systems, Minneapolis, Minn.), according to the manufacturer's instructions.

Antibody assays. Mice were bled 21 days after KBG immunization, and their sera were collected. Total IgE and antigen-specific IgG1 and IgG2a were estimated by ELISA through use of purified antimouse mABs (PHARMINGEN, San Diego, Calif.). Microtiter plates (COSTAR, Cambridge, Mass.) were coated overnight with 0.1 μg per well of purified KBG allergen in a bicarbonate buffer (0.05 mol/L, pH 9.6) or antimouse IgE mAbs. Wells were washed with washing buffer (0.5% Tween-20 in PBS, pH 7.4) and blocked with 200 μL per well of PBS (pH 7.4) containing 1% BSA for 1 hour at 37° C. After 3 washes, serum samples were added at 100 μL per well and incubated for 2 hours at 37° C. After washing, biotinylated antimouse IgG1, IgG2a, and IgE antibodies were added to each well and incubated at 37° C. for 1 hour. Streptavidin-peroxidase conjugate (1:10,000 dilution, SIGMA CHEMICALS, St Louis, Mo.) was added after washing, and the wells were further incubated at 37° C. for 1 hour. Finally, the plates were washed and color was developed by the addition of substrate tetramethyl benzidine (PHARMINGEN) at room temperature for 30 minutes. The reaction was stopped and the absorbance read at 450 nm through use of an automated ELISA reader.

Pulmonary function. To assess pulmonary function, naive mice (n=4) were vaccinated 3 times as described in connection with the vaccination protocol. Seven days after the last cytokine pDNA and KBG vaccinations, animals were sensitized intraperitoneally with 10 μg of KBG allergen and 1 mg of alum. Ten days later, these mice were challenged intranasally with 50 μg of KBG allergen once daily for 3 consecutive days. Airway responsiveness was measured with a whole-body plethysmograph (BUXCO ELECTRONICS, Troy, N.Y.) in conscious, unrestrained mice at 24 hours after allergen challenge; response to methacholine was expressed as enhanced pause, as previously described (Matsuse, H. et al., *J. Immunol.*, 2000, 164:6583-6592).

Histologic analysis. Mice were killed with an overdose (0.6 g/kg) of pentobarbital (NEMBUTAL, Abbott Laboratories, North Chicago, Ill.) 24 hours after the final allergen challenge, and lung sections were subjected to paraffin embedding. Lung inflammation was assessed after the sections were stained with hematoxylin and eosin; this was followed by scoring for severity of inflammation on a scale of 0 to 3 (0=minimum degree of inflammation; 3=the maximum), as described previously (Kumar, M. et al., *Vaccine*, 1999, 18:558-567). Pathologic scores were expressed as means±SDs. The slides were coded and scored in a blinded fashion twice each by 3 different individuals. Intraobserver variation was <5%.

Statistical analysis. Pairs of groups were compared through use of Student t tests. Differences between groups were considered significant at P<0.05. Values for all measurements are expressed as means±SDs.

EXAMPLE 1

Plasmid Constructs and Expression of IL-12 and IFN-γ

Figure 1C:
Figure 1B:
Figure 1D:
Figure 1E:
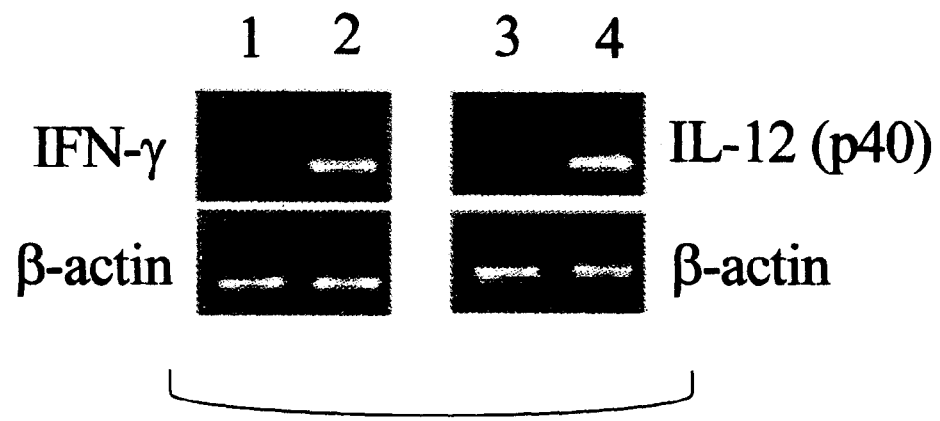

The 2 subunits of murine IL-12, p35 and p40, were cloned into the same pcDNA3.1 vector. The cloning strategy was such that each subunit was under the transcriptional control of an individual CMV immediate-early promoter and also had its own BGH poly A sequences derived from the vector pcDNA3.1. Mice given pIFN-γ or pIL-12 exhibited expression of the IFN-γ or IL-12 p40 subunit, respectively, in their muscle, as observed by immunohistochemical staining of the muscle tissues (FIGS. 1A and 1C). No immunostaining was observed in a control group of mice that received the empty vector pcDNA3.1 (FIGS. 1B and 1D). The results of RT-PCR analyses of muscle mRNAs revealed that mice given either pIFN-γ or pIL-12 (FIG. 1E, lane 2 and lane 4), but not the control group of mice (FIG. 1E, lane 1 and lane 3), expressed IFN-γ and IL-12 p40 subunit-specific mRNAs, respectively.

EXAMPLE 2

Figure 2A:
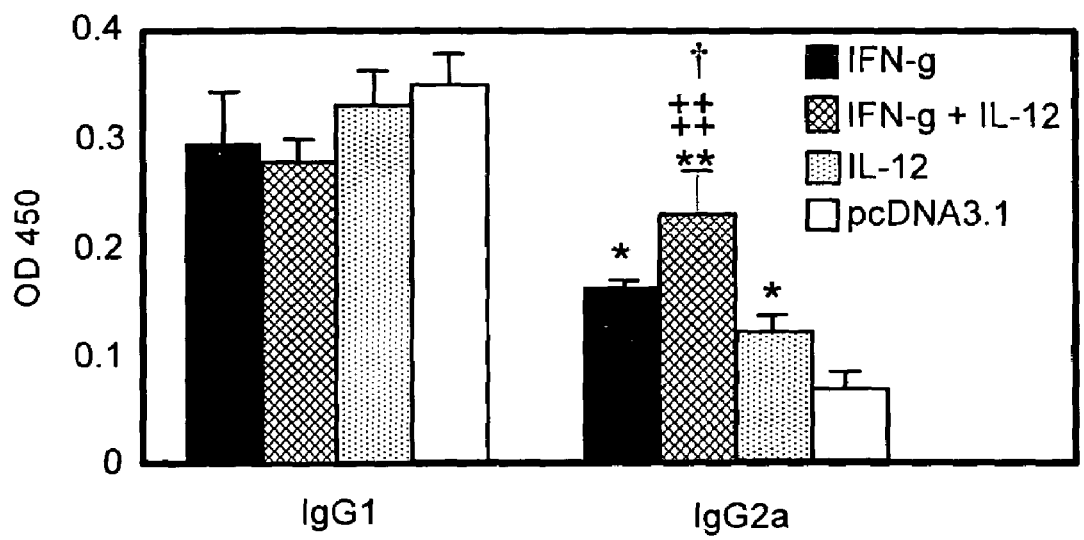
FIGS. 2A-2B show analysis of the total IgE and KBG-specific IgG subtypes. Four groups of mice (n=6) were vaccinated as described in the Methods section. On day 21, after immunization with alum and KBG allergen, their serum was analyzed for total IgE (FIG. 2B) and KBG-specific IgG2a and IgG1 (FIG. 2A) antibodies by ELISA. Bars represent the means±SDs. *P<0.05; P<0.01; *P<0.001 in comparison with pcDNA3.1 group. †P<0.05; ††P<0.01; †††P<0.001 in comparison with pIFN-γ. ‡P<0.05; ‡‡P<0.01; ‡‡‡P<0.001 in comparison with pIL-12 group.
Figure 2B:
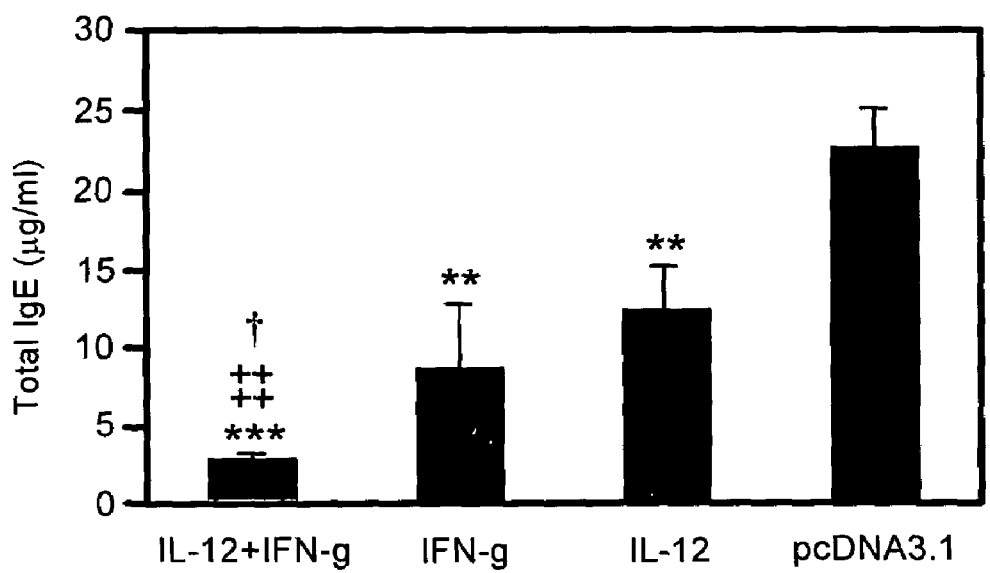

Cytokine Genetic Adjuvants Inhibit Production of IgE Antibodies and Enhanced Production of IgG2a Antibodies Four groups of mice (n=6) were vaccinated 3 times, as described in connection with the vaccination protocol. Sera were collected on day 21 after KBG immunization for an antibody assay. As shown in FIGS. 2A and 2B, mice given cytokine plasmid(s) as an adjuvant exhibited significantly lower total IgE levels than control mice (P<0.01). The group of mice given both pIL-12 and pIFN-γ constructs revealed a significantly lower amount of total IgE than mice given pIL-12 (P<0.01) or pIFN-γ (P<0.05) alone (FIG. 2B). There was also an increase in antigen-specific IgG2a levels (P<0.01) in mice given pIFN-γ plus pIL-12 as an adjuvant in comparison with the control mice and the mice receiving either plasmid alone (FIG. 2A). However, no significant difference was observed for antigen-specific IgG1 antibody levels among the cytokine pDNA-vaccinated and control groups of mice (FIG. 2A). These results indicate that administration of cytokine pDNA adjuvants along with allergen vaccines resulted in a shift in the antibody production from the IgE type to the IgG2a type.

EXAMPLE 3

Cytokine Genetic Adjuvants Alter the Cytokine Profiles of Splenocytes

Four groups of mice (n=6) were vaccinated 3 times as described in connection with the vaccination protocol. Spleens were removed on day 7, after KBG immunization, and cultured in vitro for assessment of $T_H1$-like cytokines IL-2 and IFN-γ or $T_H2$-like cytokine IL-4. Mice given cytokine pDNA adjuvants produced more $T_H1$-like cytokines than did the controls (FIGS. 3A-3C). Mice given combined pIFN-γ and pIL-12 produced higher amounts of IFN-γ (194.64 pg/mL) than mice given pIFN-γ (100.14 pg/mL) or pIL-12 (111.87 pg/mL) alone. Control mice produced only 11.71 pg/mL IFN-γ (FIG. 3A). Mice vaccinated with pDNA cytokine(s) adjuvant produced more IL-2 than did control mice. IL-2 levels after vaccinations were as follows: pIFN-γ, 73.68 pg/mL; pIL-12, 128.43 pg/mL; pIFN-γ plus pIL-12, 202.57 pg/mL; and pcDNA3.1 (control), 51.88 pg/mL (FIG. 3A). In contrast, control mice, which were vaccinated only with the empty vector plasmid, produced more IL-4 (37.55 pg/mL) than the groups injected with the pDNA cytokine adjuvant, which produced 9.71 pg/mL (pIFN-γ plus pIL-12), 13.05 pg/mL (pIFN-γ) and 17.99 pg/mL (pIL-12) of IL-4 (FIG. 3B). No significant difference was observed in IL-4 production among the pIFN-γ, pIL-12, and pIFN-γ plus pIL-12 treatment groups.

To examine the dominant pattern of cytokine responses, IFN-γ:IL-4 and IL-2:IL-4 ratios were compared among different groups of mice (FIG. 3C). The IFN-γ:IL-4 ratios in the mice vaccinated with pIFN-γ, pIL-12, and pIFN-γ plus pIL-12 as adjuvants were 7.48, 6.33, and 20.86, respectively, whereas the empty pcDNA3.1-vaccinated control exhibited a ratio of only 0.31. The ratios of IL-2:IL-4 in pIFN-γ, IL-12, pIFN-γ plus IL-12, and pcDNA3.1 controls were 7.50, 7.32, 21.71, and 1.4, respectively. These results indicate that the net cytokine balance shifted in favor of the $T_H1$-like response in cytokine plasmid-vaccinated mice; however, this shift was greater in the group vaccinated with the adjuvant that was a combination of pIFN-γ and pIL-12 plasmid DNAs.

EXAMPLE 4

Figure 4:
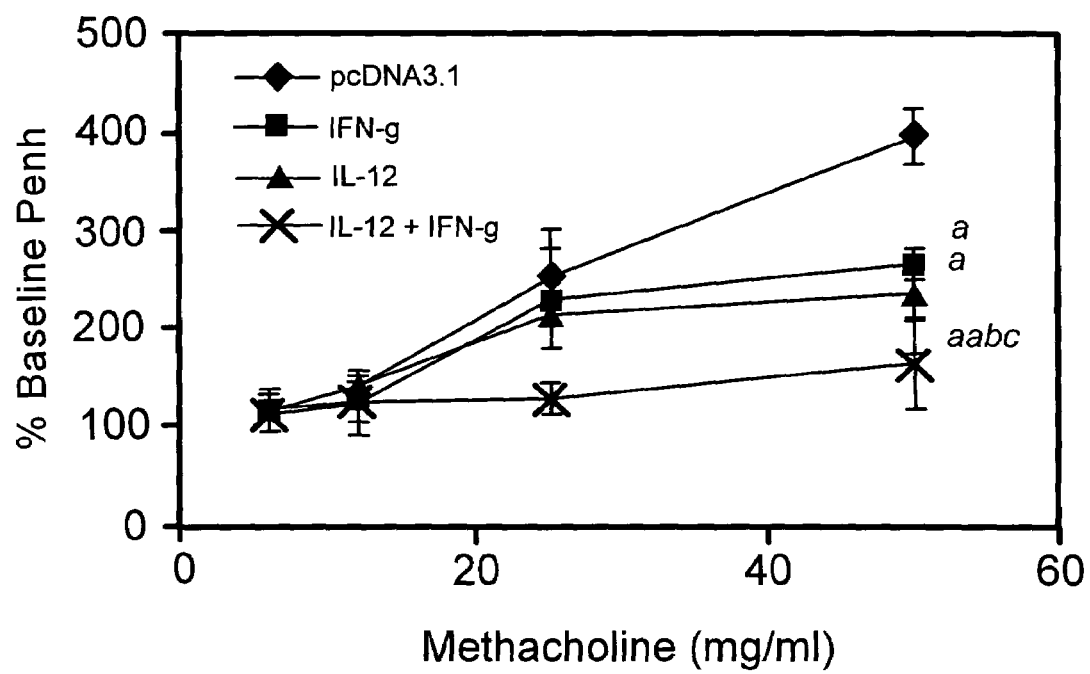
FIG. 4 shows measurement of the airway hyperresponsiveness in KBG-sensitized and -challenged mice after cytokine DNA vaccination. Naive mice (n=4) were vaccinated as described in the Methods section and sensitized with the allergen 7 days later. Ten days after the sensitization, animals were challenged intranasally 3 times with 50 μg of KBG allergen. Airway reactivity to inhaled methacholine (6 to 50 mg/mL) was measured 24 hours later. Results are expressed as means±SDs of enhanced pause values. a, P<0.05; aa, P<0.01 in comparison with pcDNA3.1 group. b and c, P<0.05 in comparison with pIFN-γ (IFN-g) and pIL-12 (IL-12) groups, respectively.

Cytokine Genetic Adjuvants Prevent the Development of Airway Hyperresponsiveness in Allergen-Sensitized and -Challenged Mice Mice (n=4) were vaccinated, sensitized, and challenged as described in connection with pulmonary function. The airways of control mice that received the empty vector as vaccine adjuvant were significantly more reactive to 50 mg/mL of methacholine than those of the mice that received pIFN-γ and/or pIL-12, as shown in FIG. 4. Mice vaccinated with pIFN-γ plus pIL-12 exhibited the least reactivity to the inhaled methacholine challenge in comparison with the pcDNA3.1 (P<0.01), pIFN-γ, and pIL-12 groups (P<0.05). These results suggest that the vaccination of mice with combined pIFN-γ and pIL-12 as an adjuvant significantly reduces airway reactivity.

EXAMPLE 5

Figure 5A:
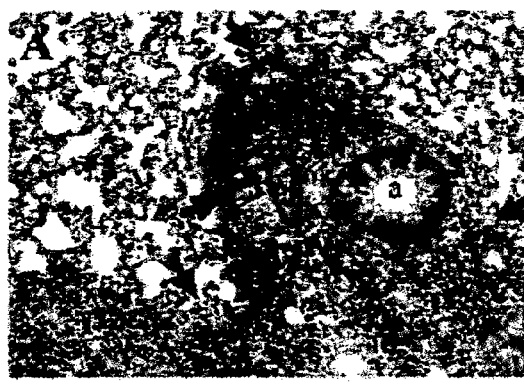
FIGS. 5A-5D show assessment of the lung inflammation in KBG-sensitized and -challenged mice after cytokine DNA vaccination. Lung tissue was removed from the different groups of mice (n=4) 24 hours after the last intranasal allergen challenge and was stained with hematoxylin and eosin. A representative photomicrograph from each group is shown (FIG. 5A: pcDNA3.1.
Figure 5B:
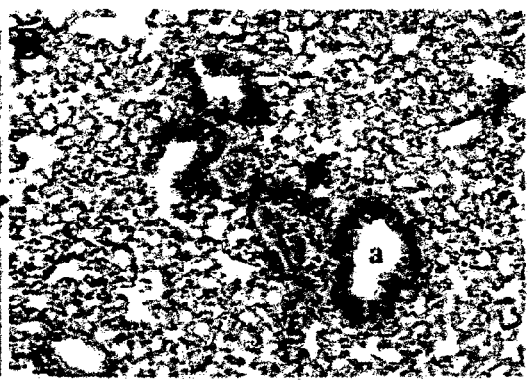
Figure 5C:
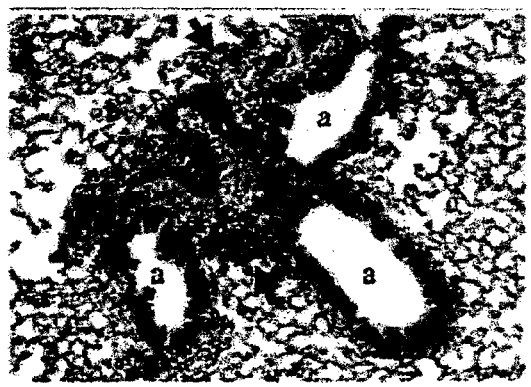
Figure 5D:
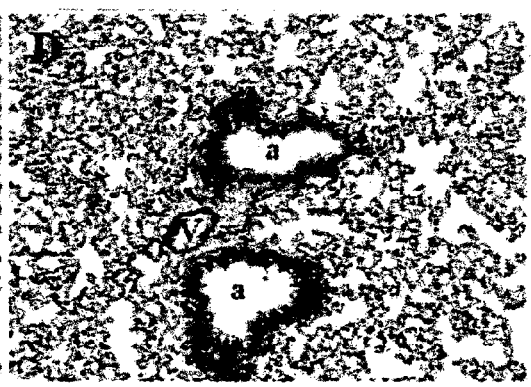

Combination of IFN-γ and IL-12 Plasmid DNAs Prevents Lung Inflammation in the Allergen-Sensitized Mice Mice (n=4) were vaccinated, sensitized, and challenged as described in connection with pulmonary function. Lung inflammation was examined 24 hours after the final allergen challenge. Representative pathologic features are shown in FIGS. 5A-5D. The group of mice receiving the combined constructs as an adjuvant (FIG. 5D) exhibited less epithelial damage and less infiltration of mononuclear cells and polymorphs in the interstitial and peribronchovascular region than was seen in the control group (FIG. 5A) and the other vaccinated groups (FIGS. 5B and 5C). A semi-quantitative analysis using a scoring system for inflammatory cells in the lung is shown in Table 1. Groups of mice that received pIFN-γ, pIL-12, or a combination of the two exhibited reduced pulmonary inflammation in comparison with the empty vector (pcDNA3.1) control. The group of mice that received the combination of pIFN-γ and pIL-12 showed significantly less (P<0.05) pulmonary inflammation than the pIFN-γ and pIL-12 groups. No statistically significant difference was found between the pIFN-γ and pIL-12 groups.

TABLE 1

Quantification of pulmonary inflammation in mice after allergen vaccination with various cytokine adjuvants

| Pathology | pcDNA3.1 | Adjuvants pIFN-γ | pIL-12 | pIFN-γ + pIL-12 |
|---|---|---|---|---|
| Epithelial damage | 2.8 ± 0.12 | 2.23 ± 0.23* | 2.3 ± 0.16* | 1.36 ± 0.48*†‡ |
| Interstitial-alveolar infiltrate | 2.73 ± 0.20 | 2.4 ± 0.25* | 2.56 ± 0.42 | 1.76 ± 0.36*†‡ |
| Peribronchovascular infiltrate | 2.83 ± 0.26 | 2.16 ± 0.23* | 2.16 ± 0.32* | 1.26 ± 0.20*†‡ |

Each value represents the mean±SD of 5 fields from 6 individual lung sections from each mouse in a group (n=4). Values were considered significant when the P value was less than 0.05 (*†‡). Statistical differences are indicated as follows: * in comparison with pcDNA3.1 control; † in comparison with pIFN-γ control; ‡ in comparison with pIL-12 control.

Previously, it was shown in a mouse model that effective parenteral vaccination of mice with grass allergens required subcutaneous injection of a high dose (250 μg to 1 mg per mouse) of allergens (Cao, Y. et al., *Immunology*, 1997, 90:46-51). By corollary, an even higher dose of allergen mixture would be required to induce an effective immune deviation from an allergic response. The results of this study demonstrate that in a mouse, a substantially lower dosage (50 μg) of allergens, when administered along with a pDNA cytokine(s) adjuvant, can induce effective immune deviation and a protective airway response in comparison with allergens alone. Furthermore, a comparison of pIFN-γ and/or pIL-12 as adjuvants indicates that the combination of pIFN-γ and pIL-12 is a more effective adjuvant than either of these plasmids alone. Although the effect of these adjuvants in mice with an established allergic response was not examined, a number of studies have reported the effectiveness of IFN-γ and of IL-12 in modulating established allergic responses (Li, X. M. et al., *J. Immunol*, 1996, 157:3216-3219; Hogan, S. P. et al., *Eur J Immunol*, 1998, 28:413-423; Dow, S. W. et al., *Hum Gene Ther*, 1999, 10:1905-1914; Maecker, H. T. et al., *J Immunol*, 2001, 166:959-965). The results of the study, therefore, have significant implications for "time-honored" AIT, which might be rendered more safe and effective by including these cytokine plasmids as adjuvants.

A major finding of this study is that a vaccine adjuvant comprising both pIFN-γ and pIL-12 inhibited total IgE levels in mice with a concomitant increase of allergen-specific IgG2a antibody production. The level of IgE synthesis in mice vaccinated with a cocktail adjuvant was significantly (P<0.001) more suppressed than that of levels obtained by vaccination with pIFN-γ or pIL-12 alone as an adjuvant. Both systemic and local IFN-γ gene delivery has been shown to decrease serum IgE levels (Dow, S. W. et al., *Hum Gene Ther*, 1999, 10:1905-1914), whereas the role of the IL-12 protein as an adjuvant on serum IgE levels has been controversial (Kips, J. C. et al., *Am J Respir Crit Care Med*, 1996, 153:535-539; Brusselle, G. G. et al., *Am. J Respir Cell Mol Biol*, 1997, 17:767-771; Sur, S. et al., *J Immunol*, 1996, 157:4173-4180; Yoshimoto, T. et al., *Proc Natl Acad Sci USA*, 1997, 94:3948-3953). The results of this study indicate that an adjuvant comprising the IFN-γ and IL-12 plasmids enhances the production of IFN-γ. This finding is in agreement with a report that mice vaccinated with IL-12 exhibited enhanced local IFN-γ production (Schwarze, J. et al., *J Allergy Clin Immunol*, 1998, 102:86-93).

The deviation of the cytokine production profile from $T_H2$-like to $T_H1$-like is a significant marker of the effectiveness of a vaccine. Analysis of the cytokine pattern of mice after vaccination with allergens and different plasmid adjuvants revealed that the group of mice receiving pIFN-γ plus pIL-12 as the adjuvant had a more profound $T_H1$-like effect—i.e., it produced higher levels of IFN-γ and IL-2 than either of the cytokine plasmids alone. Analysis of the IL-4 expression from the splenocytes of different groups of mice revealed no significant difference among the groups of mice vaccinated with pIFN-γ, pIL-12, or a combination of the two. A predominance of the $T_H1$-like response seen with cytokine adjuvants is consistent with the finding of Hogan et al. (Hogan, S. P. et al., *Eur J Immunol*, 1998, 28:413-423), who showed, using the vaccinia virus as a gene delivery vehicle, that IL-12 gene transfer to murine lung inhibited $T_H2$ cytokine production, which was mediated through the production of IFN-γ. Because allergic individuals produce limited amounts of IFN-γ, an adjuvant providing the expression of both IFN-γ and IL-12 induces a more effective $T_H1$-like response.

In patients with allergic asthma, it was shown that airway hyperresponsiveness correlates with the severity of disease and is therefore a major clinical feature of allergic asthma. A direct instillation into the respiratory tract or an intraperitoneal administration of either rIL-12 or rIFN-γ inhibits allergic airway inflammation and in some cases suppresses airway hyperresponsiveness (Gavett, S. H. et al., *J Exp Med*, 1995, 182:1527-1536; Iwamoto, I. et al., *J Exp Med*, 1993, 177:573-576). However, these protocols require a regular or daily dosing over periods ranging from 5 to 13 days to produce significant protective effects. Furthermore, gene transfer studies using IFN-γ and IL-12 have been shown to suppress airway hyperreactivity (Li, X. M. et al., *J Immunol*, 1996, 157:3216-3219; Hogan, S. P. et al., *Eur J Immunol*, 1998, 28:413-423). The results of this investigation indicate that allergen vaccine formulations that include allergens and pIFN-γ, pIL-12, or a combination of both cytokines as an adjuvant significantly decrease airway hyperresponsiveness and that a combination of pIFN-γ and pIL-12 induces the highest reduction in airway responsiveness. There appears to be a synergistic effect when both cytokine plasmids (pIFN-γ and pIL-12) are administered to the mice. A parenteral administration of only 50 μg of allergen-induced massive cellular infiltration and airway obstruction in the lung tissue of mice in the present study. However, allergens given with pIFN-γ, pIL-12, or a combination as an adjuvant limited not only the cellular infiltration but also epithelial cell damage. Consistent with previous observations, either pIFN-γ or pIL-12 as an adjuvant decreased eosinophilic cellular infiltration (Li, X. M. et al., *J Immunol*, 1996, 157:3216-3219; Hogan, S. P. et al., *Eur J Immunol*, 1998, 28:413-423), whereas treatment with a combination of pIFN-γ and pIL-12 as an adjuvant was most effective.

Not wishing to be bound by theory, one mechanism for the effectiveness of pIFN-g and pIL-12 as an adjuvant may be that CpG sequences, which are present in the backbone plasmid pcDNA3.1, nonspecifically contribute to the endogenous IL-12/IFN-g production (Roman, M. et al., *Nat Med*, 1997, 3:849-854). One possibility is that CpG sequences present in the backbone plasmid, pcDNA3.1, nonspecifically contribute to the endogenous IL-12/IFN-γ production (Roman, M. et al., *Nat Med*, 1997, 3:849-854). However, this is unlikely, because all groups received an equal dose of plasmid and mice receiving both pIFN-γ and pIL-12 received an adjusted dose (50 μg each, for a total of 100 μg). The empty vector, which also contained CpGs, had no cytokine-inducing or immunomodulatory effect. Furthermore, the higher effectiveness of combined pIFN-γ and pIL-12 in comparison with either of the plasmids alone (100 μg) might be attributed to the CpG motifs in the coding sequences; however, the cDNA inserts are mammalian sequences, which have a low frequency of CpG dinucleotides, are mostly methylated, and do not have immunostimulatory activity (Hemmi, H. et al., *Nature*, 2000, 408:740-750). Nonetheless, a search for a canonical hexamer purine-purine-CG-pyrimidine-pyrimidine as a possible core CpG motif led to the identification of GACGTT, GGCGTC, GGCGTT sequences in IL-12, and AACGCT, AGCGCT sequences in IFN-γ. However, whether these sequences in the mouse cDNA are capable of binding to the mouse Toll-like receptor 9 and cause immune stimulation, like the CpG motifs present in the bacterial DNA, remains to be investigated (Hemmi, H. et al., *Nature*, 2000, 408:740-750).

Alternatively, the synergy between pIFN-γ and pIL-12 on the induction of a $T_H1$-dominant state and the inhibition of airway inflammation may be in their cellular mechanism of action. First, although IL-12 is the primary determinant of the $T_H1$ differentiation, IFN-γ endogenously synthesized during the priming of naive CD4-positive T cells both accelerates and enhances the $T_H1$ differentiating effects of IL-12 (Wenner, C. A. et al., *J Immunol*, 1996, 56:1442-1447; Bradley, L. M. et al., *J Immunol*, 1996, 157:1350-1358). Thus, IFN-γ presumably synergizes with T-cell receptor engagement and induces the expression of functional IL-12 receptors on naive T cells. This idea is consistent with the report that the presence of IFN-γ and IFN-α in cultures enhanced IL-12Rβ2 expression on CD4-positive and CD8-positive T cells and that the enhancing effect of IFN-γ was independent of endogenous IL-12 or IFN-α (Wu, C. Y. et al., *Eur J Immunol*, 2000, 30:1364-1374). Second, the highest amount of IL-2 produced by a combined vaccination with pIFN-γ and pIL-12 might synergize with IFN-γ effects and contribute to a more effective $T_H1$-like response. IL-2 regulates expression of the IL-12β2 receptor on natural killer cells (Wu, C. Y. et al., *Eur J Immunol*, 2000, 30:1364-1374). It is to be noted however, that these 2 possibilities are not mutually exclusive. Irrespective of the mechanism involved, the results lead to the conclusion that in a mouse model of grass allergy, the administration of cytokine plasmids encoding IFN-γ and IL-12 as an adjuvant enhances the therapeutic effectiveness of grass allergen vaccines.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A method for modulating an immune response, comprising co-administering to a mammal:
   an effective amount of a nucleic acid sequence encoding p35 and p40 subunits of human IL-12, and a promoter sequence operably linked to the nucleic acid sequence encoding the p35 and p40 subunits;
   an effective amount of a nucleic acid sequence encoding human IFN-γ, and a promoter sequence operably linked to the nucleic acid sequence encoding human IFN-γ; and
   an antigen, such that the co-administering results in an increase of IFN-γ and IL-2 production, an increase of IgG2a specific to the antigen, a decrease of IL-4 production, and reduced serum IgE.

2. The method of claim 1, wherein the co-administering results in expression of the p35 and p40 subunits, the p35 subunit comprising the amino acid sequence of SEQ ID NO:8, and the p40 subunit comprising the amino acid sequence of SEQ ID NO:10.

3. The method of claim 1, wherein the co-administering results in expression of the human IFN-γ, and wherein the human IFN-γ comprises the amino acid sequence of SEQ ID NO:12.

4. The method of claim 1, wherein the nucleic acid sequence encoding the p35 and the p40 subunits of the human IL-12 comprises SEQ ID NO:7 and SEQ ID NO:9.

5. The method of claim 1, wherein the nucleic acid sequence encoding the human IFN-γ comprises SEQ ID NO:11.

6. The method of claim 1, wherein the nucleic acid sequences are administered with a pharmaceutically acceptable carrier.

7. The method of claim 1, wherein the nucleic acid sequences and promoter sequences are administered within a viral vector.

8. The method of claim 1, wherein the antigen is selected from the group consisting of a protein, peptide, glycoprotein, carbohydrate, lipid, glycolipid, hapten conjugate, recombinant, nucleotides, killed or attenuated organism, toxin, toxoid, and organic molecule.

9. The method of claim 1, wherein the antigen is administered to the mammal with the nucleic acid sequences and a pharmaceutically acceptable carrier.

10. The method of claim 1, wherein the mammal is human.

11. A method for modulating an immune response, comprising co-administering to a mammal:
    an effective amount of a plasmid comprising a nucleic acid sequence encoding p35 and p40 subunits of human IL-12, and a promoter sequence operably linked to the nucleic acid sequence encoding the p35 and p40 subunits;
    an effective amount of a plasmid comprising a nucleic acid sequence encoding human IFN-γ, and a promoter sequence operably linked to the nucleic acid sequence encoding the human IFN-γ; and
    an antigen, such that the co-administering results in an increase of IFN-γ and IL-2 production, an increase of IgG2a specific to the antigen, a decrease of IL-4 production, and reduced serum IgE.

12. The method of claim 11, wherein the antigen comprises an allergen.

13. The method of claim 11, wherein the antigen comprises Kentucky blue grass (KBG) allergen extract.

14. The method of claim 11, wherein the operably linked promoter sequences comprise cytomegalovirus (CMV) promoters.

15. The method of claim 11, wherein the antigen comprises Kentucky blue grass (KBG) allergen extract, and the operably linked promoter sequences comprise cytomegalovirus (CMV) promoters.

16. The method of claim 11, wherein the mammal is human.

17. The method of claim 11, wherein the co-administering results in expression of the p35 and the p40 subunits, the p35 subunit comprising the amino acid sequence of SEQ ID NO:8, and the p40 subunit comprising the amino acid sequence of SEQ ID NO:10.

18. The method of claim 11, wherein the mammal suffers from a condition selected from the group consisting of allergy, allergic rhinitis, atopic dermatitis, asthma, allergic sinusitis, pulmonary fibrosis, and cancer.

19. The method of claim 11, wherein the plasmids are administered by a route selected from the group consisting of intramuscularly, orally, and intranasally.

20. The method of claim 1, wherein the nucleic acid sequence encoding the p35 and p40 subunits of the human IL-12 and the nucleic acid sequence encoding the human IFN-γ are co-administered to the mammal through a mucosal route.

21. The method of claim 1, wherein the nucleic acid sequence encoding the p35 and p40 subunits of the human IL-12 and the nucleic sequence encoding the human IFN-γ are co-administered to the mammal intranasally.

22. The method of claim 11, wherein the plasmids are co-administered to the mammal through a mucosal route.

23. The method of claim 11, wherein the plasmids are co-administered to the mammal intranasally.

24. The method of claim 1, wherein the mammal suffers from a condition selected from the group consisting of allergy, allergic rhinitis, atopic dermatitis, asthma, allergic sinusitis, pulmonary fibrosis, and cancer.

25. The method of claim 11, wherein the nucleic acid sequence encoding the p35 and p40 subunits of human IL-12 comprises SEQ ID NO: 7 and SEQ ID NO: 9.

26. The method of claim 11, wherein the nucleic acid sequence encoding human IFN-γ comprises SEQ ID NO: 11.

27. The method of claim 1, wherein the nucleic acid sequences are administered by a route selected from the group consisting of intramuscularly, orally, and intranasally.

28. The method of claim 1, wherein said co-administering is carried out intramuscularly.

29. The method of claim 11, wherein said co-administering is carried out intramuscularly.

30. The method of claim 1, wherein the nucleic acid sequences are conjugated with chitosan to form nanoparticles.

31. The method of claim 11, wherein the plasmids are conjugated with chitosan to form nanoparticles.

* * * * *

UNITED STATES PATENT AND TRADEMARK OFFICE
CERTIFICATE OF CORRECTION

PATENT NO. : 7,595,303 B1
APPLICATION NO. : 10/655873
DATED : September 29, 2009
INVENTOR(S) : Shyam S. Mohapatra and Mukesh Kumar It is certified that error appears in the above-identified patent and that said Letters Patent is hereby corrected as shown below:

Title Page, (57) Abstract,
Line 13, "cells generally modified" should read --cells genetically modified--.

Column 3,
Line 32, "a, airway;" should read --$a$, airway;--.

Column 7,
Line 9, "parental administration" should read --parenteral administration--.

Column 9,
Line 38, "ctgtcaatta" should read --ctgtgcctta--.
Line 54, "ttttactgaa" should read --ttttcatgaa--.

Column 10,
Line 5, "YKTKLHA" should read --YKTKIKLCILLHA--.

Column 33,
Lines 61-62, "recombinant, nucleotides," should read --recombinant nucleotides,--.

Signed and Sealed this

Second Day of February, 2010

David J. Kappos
*Director of the United States Patent and Trademark Office*

SEQUENCE LISTING

```
<160> NUMBER OF SEQ ID NOS: 12

<210> SEQ ID NO 1
<211> LENGTH: 23
<212> TYPE: DNA
<213> ORGANISM: Artificial Sequence
<220> FEATURE:
<223> OTHER INFORMATION: forward primer for murine IL-12 p40 subunit

<400> SEQUENCE: 1
ccaggcagct agcagcaaag caa                                            23

<210> SEQ ID NO 2
<211> LENGTH: 26
<212> TYPE: DNA
<213> ORGANISM: Artificial Sequence
<220> FEATURE:
<223> OTHER INFORMATION: reverse primer for murine IL-12 p40 subunit
```

```
<400> SEQUENCE: 2
tccctcgagg catcctagga tcggac                                           26

<210> SEQ ID NO 3
<211> LENGTH: 22
<212> TYPE: DNA
<213> ORGANISM: Artificial Sequence
<220> FEATURE:
<223> OTHER INFORMATION: forward primer for plasmid pc40

<400> SEQUENCE: 3
acccaagctt gctagcagca aa                                               22

<210> SEQ ID NO 4
<211> LENGTH: 23
<212> TYPE: DNA
<213> ORGANISM: Artificial Sequence
<220> FEATURE:
<223> OTHER INFORMATION: reverse primer for plasmid pc40

<400> SEQUENCE: 4
gaagccatag agggtaccgc atc                                              23

<210> SEQ ID NO 5
<211> LENGTH: 22
<212> TYPE: DNA
<213> ORGANISM: Artificial Sequence
<220> FEATURE:
<223> OTHER INFORMATION: forward primer for murine IL-12 p35 subunit

<400> SEQUENCE: 5
tgcggatcca gcatgtgtca at                                               22

<210> SEQ ID NO 6
<211> LENGTH: 22
<212> TYPE: DNA
<213> ORGANISM: Artificial Sequence
<220> FEATURE:
<223> OTHER INFORMATION: reverse primer for murine IL-12 p35 subunit

<400> SEQUENCE: 6
gcagagggcc tcgagctttc ag                                               22

<210> SEQ ID NO 7
<211> LENGTH: 1444
<212> TYPE: DNA
<213> ORGANISM: Homo sapiens

<400> SEQUENCE: 7
tttcattttg ggccgagctg gaggcggcgg ggccgtcccg gaacggctgc ggccgggcac      60
cccgggagtt aatccgaaag cgccgcaagc ccgcgggcc ggccgcaccg cacgtgtcac      120
cgagaagctg atgtagagag agacacagaa ggagacagaa agcaagagac cagagtcccg     180
ggaaagtcct gccgcgcctc gggacaatta taaaaatgtg gcccctggg tcagcctccc      240 agccaccgcc ctcacctgcc gcggccacag gtctgcatcc agcggctcgc cctgtgtccc     300
tgcagtgccg gctcagcatg tgtccagcgc gcagcctcct ccttgtggct accctggtcc     360
tcctggacca cctcagtttg gccagaaacc tccccgtggc cactccagac ccaggaatgt     420
tcccatgcct tcaccactcc caaaacctgc tgagggccgt cagcaacatg ctccagaagg     480
ccagacaaac tctagaattt tacccttgca cttctgaaga gattgatcat gaagatatca     540
caaaagataa aaccagcaca gtggaggcct gtttaccatt ggaattaacc aagaatgaga     600
```

-continued

```
gttgcctaaa ttccagagag acctctttca taactaatgg gagttgcctg gcctccagaa      660
agacctcttt tatgatggcc ctgtgcctta gtagtattta tgaagacttg aagatgtacc      720
aggtggagtt caagaccatg aatgcaaagc ttctgatgga tcctaagagg cagatctttc      780
tagatcaaaa catgctggca gttattgatg agctgatgca ggccctgaat tcaacagtg       840 agactgtgcc acaaaaatcc tcccttgaag aaccggattt ttataaaact aaaatcaagc      900
tctgcatact tcttcatgct ttcagaattc gggcagtgac tattgataga gtgatgagct      960
atctgaatgc ttcctaaaaa gcgaggtccc tccaaaccgt tgtcattttt ataaaacttt     1020
gaaatgagga aactttgata ggatgtggat taagaactag ggaggggaa agaaggatgg      1080 gactattaca tccacatgat acctctgatc aagtattttt gacatttact gtggataaat     1140 tgttttaag ttttcatgaa tgaattgcta agaagggaaa atatccatcc tgaaggtgtt     1200
tttcattcac tttaatagaa gggcaaatat ttataagcta tttctgtacc aaagtgtttg     1260
tggaaacaaa catgtaagca taacttattt taaaatattt atttatataa cttggtaatc     1320
atgaaagcat ctgagctaac ttatatttat ttatgttata tttattaaat tatttatcaa     1380
gtgtatttga aaaatatttt taagtgttct aaaaataaaa gtattgaatt aaagtgaaaa     1440
aaaa                                                                  1444
```

<210> SEQ ID NO 8
<211> LENGTH: 253
<212> TYPE: PRT
<213> ORGANISM: Homo sapiens

<400> SEQUENCE: 8

```
Met Trp Pro Pro Gly Ser Ala Ser Gln Pro Pro Ser Pro Ala Ala
1               5                   10                  15

Ala Thr Gly Leu His Pro Ala Ala Arg Pro Val Ser Leu Gln Cys Arg
            20                  25                  30

Leu Ser Met Cys Pro Ala Arg Ser Leu Leu Val Ala Thr Leu Val
        35                  40                  45

Leu Leu Asp His Leu Ser Leu Ala Arg Asn Leu Pro Val Ala Thr Pro
    50                  55                  60

Asp Pro Gly Met Phe Pro Cys Leu His His Ser Gln Asn Leu Leu Arg
65                  70                  75                  80

Ala Val Ser Asn Met Leu Gln Lys Ala Arg Gln Thr Leu Glu Phe Tyr
                85                  90                  95

Pro Cys Thr Ser Glu Glu Ile Asp His Glu Asp Ile Thr Lys Asp Lys
            100                 105                 110

Thr Ser Thr Val Glu Ala Cys Leu Pro Leu Glu Leu Thr Lys Asn Glu
        115                 120                 125

Ser Cys Leu Asn Ser Arg Glu Thr Ser Phe Ile Thr Asn Gly Ser Cys
    130                 135                 140

Leu Ala Ser Arg Lys Thr Ser Phe Met Met Ala Leu Cys Leu Ser Ser
145                 150                 155                 160

Ile Tyr Glu Asp Leu Lys Met Tyr Gln Val Glu Phe Lys Thr Met Asn
                165                 170                 175

Ala Lys Leu Leu Met Asp Pro Lys Arg Gln Ile Phe Leu Asp Gln Asn
            180                 185                 190

Met Leu Ala Val Ile Asp Glu Leu Met Gln Ala Leu Asn Phe Asn Ser
        195                 200                 205

Glu Thr Val Pro Gln Lys Ser Ser Leu Glu Glu Pro Asp Phe Tyr Lys
```

|     |     |     |     |     |     |     |     |
|---|---|---|---|---|---|---|---|
| | 210 | | | 215 | | | 220 |
| Thr | Lys | Ile | Lys | Leu | Cys | Ile | Leu | Leu | His | Ala | Phe | Arg | Ile | Arg | Ala |
| 225 | | | | 230 | | | | | 235 | | | | | 240 | |
| Val | Thr | Ile | Asp | Arg | Val | Met | Ser | Tyr | Leu | Asn | Ala | Ser |
| | | | | 245 | | | | | 250 | | | |

<210> SEQ ID NO 9
<211> LENGTH: 2347
<212> TYPE: DNA
<213> ORGANISM: Homo sapiens

<400> SEQUENCE: 9

| | | | | | |
|---|---|---|---|---|---|
| ctgtttcagg | gccattggac | tctccgtcct | gcccagagca | agatgtgtca | ccagcagttg | 60 |
| gtcatctctt | ggttttccct | ggttttctg | catctcccc | tcgtggccat | atgggaactg | 120 |
| aagaaagatg | tttatgtcgt | agaattggat | tggtatccgg | atgcccctgg | agaaatggtg | 180 |
| gtcctcacct | gtgacacccc | tgaagaagat | ggtatcacct | ggaccttgga | ccagagcagt | 240 |
| gaggtcttag | gctctggcaa | aaccctgacc | atccaagtca | aagagtttgg | agatgctggc | 300 |
| cagtacacct | gtcacaaagg | aggcgaggtt | ctaagccatt | cgctcctgct | gcttcacaaa | 360 |
| aaggaagatg | gaatttggtc | cactgatatt | ttaaaggacc | agaaagaacc | caaaaataag | 420 |
| acctttctaa | gatgcgaggc | caagaattat | tctggacgtt | tcacctgctg | gtggctgacg | 480 |
| acaatcagta | ctgatttgac | attcagtgtc | aaaagcagca | gaggctcttc | tgaccccaa | 540 |
| ggggtgacgt | gcggagctgc | tacactctct | gcagagagag | tcagagggga | caacaaggag | 600 |
| tatgagtact | cagtggagtg | ccaggaggac | agtgcctgcc | cagctgctga | ggagagtctg | 660 |
| cccattgagg | tcatggtgga | tgccgttcac | aagctcaagt | atgaaaacta | caccagcagc | 720 |
| ttcttcatca | gggacatcat | caaacctgac | ccacccaaga | acttgcagct | gaagccatta | 780 |
| aagaattctc | ggcaggtgga | ggtcagctgg | gagtaccctg | acacctggag | tactccacat | 840 |
| tcctacttct | ccctgacatt | ctgcgttcag | gtccagggca | agagcaagag | agaaaagaaa | 900 |
| gatagagtct | tcacggacaa | gacctcagcc | acggtcatct | gccgcaaaaa | tgccagcatt | 960 |
| agcgtgcggg | cccaggaccg | ctactatagc | tcatcttgga | gcgaatgggc | atctgtgccc | 1020 |
| tgcagttagg | ttctgatcca | ggatgaaaat | ttggaggaaa | agtggaagat | attaagcaaa | 1080 |
| atgtttaaag | acacaacgga | atagacccaa | aaagataatt | tctatctgat | ttgctttaaa | 1140 |
| acgttttttt | aggatcacaa | tgatatcttt | gctgtatttg | tatagttaga | tgctaaatgc | 1200 |
| tcattgaaac | aatcagctaa | tttatgtata | gattttccag | ctctcaagtt | gccatgggcc | 1260 |
| ttcatgctat | ttaaatattt | aagtaattta | tgtatttatt | agtatattac | tgttatttaa | 1320 |
| cgtttgtctg | ccaggatgta | tggaatgttt | catactctta | tgacctgatc | catcaggatc | 1380 |
| agtccctatt | atgcaaaatg | tgaatttaat | tttatttgta | ctgacaactt | ttcaagcaag | 1440 |
| gctgcaagta | catcagtttt | atgacaatca | ggaagaatgc | agtgttctga | taccagtgcc | 1500 |
| atcatacact | tgtgatggat | gggaacgcaa | gagatactta | catggaaacc | tgacaatgca | 1560 |
| aacctgttga | agatccag | agaacaaga | tgctagttcc | catgtctgtg | aagacttcct | 1620 |
| ggagatggtg | ttgataaagc | aatttagggc | cacttacact | tctaagcaag | tttaatcttt | 1680 |
| ggatgcctga | ttttaaaag | ggctagaaaa | aaatgattga | ccagcctggg | aaacataaca | 1740 |
| agaccccgtc | tctacaaaaa | aaatttaaaa | ttagccaggc | gtggtggctc | atgcttgtgg | 1800 |
| tcccagctgt | tcaggaggat | gaggcaggag | gatctcttga | gcccaggagg | tcaaggctat | 1860 |
| ggtgagccgt | gattgtgcca | ctgcatacca | gcctaggtga | cagaatgaga | ccctgtctca | 1920 |

-continued

```
aaaaaaaaaa tgattgaaat taaaattcag ctttagcttc catggcagtc ctcaccccca    1980
cctctctaaa agacacagga ggatgacaca gaaacaccgt aagtgtctgg aaggcaaaaa    2040
gatcttaaga ttcaagagag aggacaagta gttatggcta aggacatgaa attgtcagaa    2100
tggcaggtgg cttcttaaca gccctgtgag aagcagacag atgcaaagaa atctggaat    2160 cccttctca ttagcatgaa tgaacctgat acacaattat gaccagaaaa tatggctcca    2220
tgaaggtgct acttttaagt aatgtatgtg cgctctgtaa agtgattaca tttgtttcct    2280
gtttgtttat ttatttattt atttttgcat tctgaggctg aactaataaa aactcttctt    2340
tgtaatc    2347
```

<210> SEQ ID NO 10
<211> LENGTH: 328
<212> TYPE: PRT
<213> ORGANISM: Homo sapiens

<400> SEQUENCE: 10

```
Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
                20                  25                  30

Val Glu Leu Asp Trp Tyr Pro Asp Ala Pro Gly Glu Met Val Val Leu
            35                  40                  45

Thr Cys Asp Thr Pro Glu Glu Asp Gly Ile Thr Trp Thr Leu Asp Gln
        50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285
```

```
Val Phe Thr Asp Lys Thr Ser Ala Thr Val Ile Cys Arg Lys Asn Ala
    290                 295                 300
Ser Ile Ser Val Arg Ala Gln Asp Arg Tyr Tyr Ser Ser Ser Trp Ser
305                 310                 315                 320
Glu Trp Ala Ser Val Pro Cys Ser
                325
```

<210> SEQ ID NO 11
<211> LENGTH: 1240
<212> TYPE: DNA
<213> ORGANISM: Homo sapiens

<400> SEQUENCE: 11

```
cacattgttc tgatcatctg aagatcagct attagaagag aaagatcagt taagtccttt      60
ggacctgatc agcttgatac aagaactact gatttcaact tctttggctt aattctctcg    120
gaaacgatga atatacaag ttatatcttg gcttttcagc tctgcatcgt tttgggttct     180
cttggctgtt actgccagga cccatatgta aagaagcag aaaaccttaa gaaatatttt     240
aatgcaggtc attcagatgt agcggataat ggaactcttt tcttaggcat tttgaagaat    300
tggaaagagg agagtgacag aaaaataatg cagagccaaa ttgtctcctt ttacttcaaa    360
cttttttaaaa actttaaaga tgaccagagc atccaaaaga gtgtggagac catcaaggaa   420
gacatgaatg tcaagttttt caatagcaac aaaaagaaac gagatgactt cgaaaagctg    480
actaattatt cggtaactga cttgaatgtc aacgcaaag caatacatga actcatccaa     540
gtgatggctg aactgtcgcc agcagctaaa acagggaagc gaaaaaggag tcagatgctg    600
tttcgaggtc gaagagcatc ccagtaatgg ttgtcctgcc tgcaatattt gaattttaaa    660
tctaaatcta tttattaata tttaacatta tttatgggg aatatatttt ttagactcat     720
caatcaaata agtatttata atagcaactt ttgtgtaatg aaaatgaata tctattaata    780
tatgtattat ttataattcc tatatcctgt gactgtctca cttaatcctt tgttttctga    840
ctaattaggc aaggctatgt gattacaagg ctttatctca ggggccaact aggcagccaa    900
cctaagcaag atcccatggg ttgtgtgttt atttcacttg atgatacaat gaacacttat    960
aagtgaagtg atactatcca gttactgccg gtttgaaaat atgcctgcaa tctgagccag   1020
tgctttaatg gcatgtcaga cagaacttga atgtgtcagg tgaccctgat gaaaacatag  1080
catctcagga gatttcatgc ctggtgcttc caaatattgt tgacaactgt gactgtaccc  1140
aaatggaaag taactcattt gttaaaatta tcaatatcta atatatatga ataaagtgta   1200
agttcacaac aaaaaaaaaa aaaaaaaaa aaaaaaaaa                          1240
```

<210> SEQ ID NO 12
<211> LENGTH: 166
<212> TYPE: PRT
<213> ORGANISM: Homo sapiens

<400> SEQUENCE: 12

```
Met Lys Tyr Thr Ser Tyr Ile Leu Ala Phe Gln Leu Cys Ile Val Leu
1               5                   10                  15
Gly Ser Leu Gly Cys Tyr Cys Gln Asp Pro Tyr Val Lys Glu Ala Glu
                20                  25                  30
Asn Leu Lys Lys Tyr Phe Asn Ala Gly His Ser Asp Val Ala Asp Asn
            35                  40                  45
Gly Thr Leu Phe Leu Gly Ile Leu Lys Asn Trp Lys Glu Glu Ser Asp
        50                  55                  60
```

```
                            -continued

Arg Lys Ile Met Gln Ser Gln Ile Val Ser Phe Tyr Phe Lys Leu Phe
65              70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165
```